United States Patent
Harper et al.

(10) Patent No.: US 9,539,325 B2
(45) Date of Patent: Jan. 10, 2017

(54) COMBINATION THERAPY FOR TREATING BREAST CANCER

(71) Applicant: Genzyme Corporation, Cambridge, MA (US)

(72) Inventors: Jay Harper, Salem, MA (US); Scott Lonning, Northbridge, MA (US); Frank Hsu, Wellesley, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/562,306

(22) Filed: Dec. 5, 2014

(65) Prior Publication Data

US 2015/0086547 A1  Mar. 26, 2015

Related U.S. Application Data

(62) Division of application No. 13/634,392, filed as application No. PCT/US2011/027589 on Mar. 8, 2011, now Pat. No. 8,911,736.

(60) Provisional application No. 61/313,515, filed on Mar. 12, 2010.

(51) Int. Cl.
| | | |
|---|---|---|
| *A61K 39/395* | (2006.01) | |
| *A61K 31/427* | (2006.01) | |
| *A61K 31/7068* | (2006.01) | |
| *A61K 31/425* | (2006.01) | |
| *A61K 31/505* | (2006.01) | |
| *A61K 31/506* | (2006.01) | |
| *A61K 38/18* | (2006.01) | |

(52) U.S. Cl.
CPC ....... *A61K 39/39558* (2013.01); *A61K 31/425* (2013.01); *A61K 31/427* (2013.01); *A61K 31/505* (2013.01); *A61K 31/506* (2013.01); *A61K 31/7068* (2013.01); *A61K 38/1841* (2013.01); *A61K 39/395* (2013.01)

(58) Field of Classification Search
None
See application file for complete search history.

(56) References Cited

U.S. PATENT DOCUMENTS

| 5,225,539 A | 7/1993 | Winter |
| 2006/0153917 A1 | 7/2006 | Ullah et al. |
| 2009/0285810 A1 | 11/2009 | Adams et al. |

OTHER PUBLICATIONS

Hu et al. A modified hTERT promoter-directed oncolytic adenovirus replication with concurrent inhibition of TGFbeta signaling for breast cancer therapy. Cancer Gene Ther. Apr. 2010;17(4):235-43.
International Preliminary Report on Patentability for International Application No. PCT/US2011/027589 dated Sep. 27, 2012.
Ling et al., Therapeutic Role of TGF-Beta Neutralizing Antibody in Mouse Cyclosporin A Nephropathy: Morpologic Improvement Associated with Functional Preservation, J Am Soc Nephrol, 2003, vol. 14, pp. 377-388.
Mourskaia et al. Transforming growth factor-beta1 is the predominant isoform required for breast cancer cell outgrowth in bone. Oncogene. Feb. 19, 2009;28(7):1005-15.
O'Shaughnessy et al. Capecitabine/Taxane combination therapy: evolving clinical utility in breast cancer. Clin Breast Cancer. Apr. 2006;7(1):42-50.
Tan et al. Transforming growth factor-beta signaling: emerging stem cell target in metastatic breast cancer? Breast Cancer Res Treat. Jun. 2009;115(3):453-95. Epub Oct. 9, 2008.
International Search Report and Written Opinion of the International Searching Authority, or the Declaration for International Application No. PCT/US11/27589 dated May 13, 2011.

*Primary Examiner* — David Romeo
(74) *Attorney, Agent, or Firm* — Mark S. Cohen; Pearl Cohen Zedek Latzer Baratz LLP

(57) ABSTRACT

The invention provides compositions and methods for treating breast cancer. Specifically, the invention relates to administering a Transforming Growth Factor beta (TGFβ) antagonist in combination with capecitabine and ixabepilone to treat breast cancer.

16 Claims, 22 Drawing Sheets

COMBINATION THERAPY FOR TREATING BREAST CANCER

CROSS-REFERENCE TO RELATED APPLICATIONS

This application is a divisional of U.S. patent application Ser. No. 13/634,392, filed Oct. 5, 2012, which is a national stage application of PCT International Application PCT/US 11/27589, filed Mar. 8, 2011, which claims priority to U.S. Provisional Patent Application 61/313,515, filed Mar. 12, 2010, all of which are incorporated by reference herein in their entirety.

FIELD OF THE INVENTION

The invention relates to compositions and methods for treating breast cancer. Specifically, the invention relates to administering a Transforming Growth Factor beta (TGFβ) antagonist in combination with one or more chemotherapy agents to treat breast cancer.

BACKGROUND OF THE INVENTION

The transforming growth factor-beta (TGF-beta or TGFβ) superfamily contains many member proteins that share common sequence elements and structural motifs. These proteins are known to elicit a wide spectrum of biological responses in a variety of cell types. Cellular signaling triggered by members of the TGFβ superfamily members involves cooperative binding of the ligand to both TGFβ Type II and Type III transmembrane receptor components, which induces assembly of an active serine/threonine kinase receptor complex with the TGFβ Type I receptor. This receptor complex initiates a signal transduction pathway by phosphorylating cytoplasmic Smad proteins, which then translocate to the nucleus and act to suppress or activate transcription of target genes.

Many TGFβ superfamily proteins have important functions during embryonic development in pattern formation and tissue specification. TGFβ superfamily protein-induced signaling regulates a variety of differentiation processes, including adipogenesis, myogenesis, chondrogenesis, hematopoiesis, and epithelial cell differentiation (for review, See Massague, 1987, *Cell* 49:437; Siegel et al., 2003, *Nature Review Cancer*, 8:807-20). In adult tissues, TGFβ superfamily proteins are also involved in processes such as tumor growth and metastasis, wound healing, bone repair, and bone remodeling. The tumor-suppressive effects of TGFβ have been demonstrated in earlier studies. See Derynck et al., 2001, *Nat Genet*, 29:117-129.

TGFβ antagonist molecules regulate TGFβ mediated signaling. Examples of such antagonists include monoclonal and polyclonal antibodies directed against one or more isoforms of TGFβ (U.S. Pat. No. 5,571,714 and PCT patent application WO 97/13844).

TGFβ antagonist molecules were found to inhibit breast cancer cell tumorigenicity and increase mouse spleen natural killer cell activity. See Arteaga et al., 1993, *J. Clin. Invest.*, 92:6.

There exists a need for combination therapy modalities to treat cancer.

SUMMARY OF THE INVENTION

The invention provides a combination therapeutic method to treat breast cancer in a subject. The method includes the steps of administering to the subject a therapeutically effective amount of a Transforming Growth Factor beta (TGFβ) antagonist in combination with capecitabine, ixabepilone, or both. The use of (TGFβ) antagonist in combination with capecitabine and ixabepilone enhances the efficacy of the combination of capecitabine and ixabepilone to treat a breast cancer.

In one embodiment, the TGFβ antagonist is a molecule that blocks the binding of a TGFβ protein to its receptor. In another embodiment, the TGFβ antagonist is a molecule that is capable of diminishing the activity of a TGFβ. In a particular embodiment, the TGFβ antagonist is an anti-TGFβ monoclonal antibody that binds to or neutralizes one or more isoforms of TGFβ (e.g., a pan-specific anti-TGFβ antibody).

In some embodiments, the TGFβ antagonist is co-administered with a combination of capecitabine and ixabepilone. In other embodiments, the TGFβ antagonist is administered independently from the administration of a combination of capecitabine and ixabepilone.

The combination therapy of the invention inhibits the growth of primary tumor and further inhibits metastasis from primary tumor to lung.

The invention also provides a pharmaceutical composition that comprises a therapeutically effective amount of a TGFβ antagonist, wherein the TGFβ antagonist is present in an amount effective to enhance the efficacy of the combination of capecitabine and ixabepilone to treat a breast cancer.

The invention further provides a kit that comprises a therapeutically effective amount of a TGFβ antagonist, wherein the TGFβ antagonist is present in an amount effective to enhance the efficacy of the combination of capecitabine and ixabepilone to treat a breast cancer.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

Figure 1:
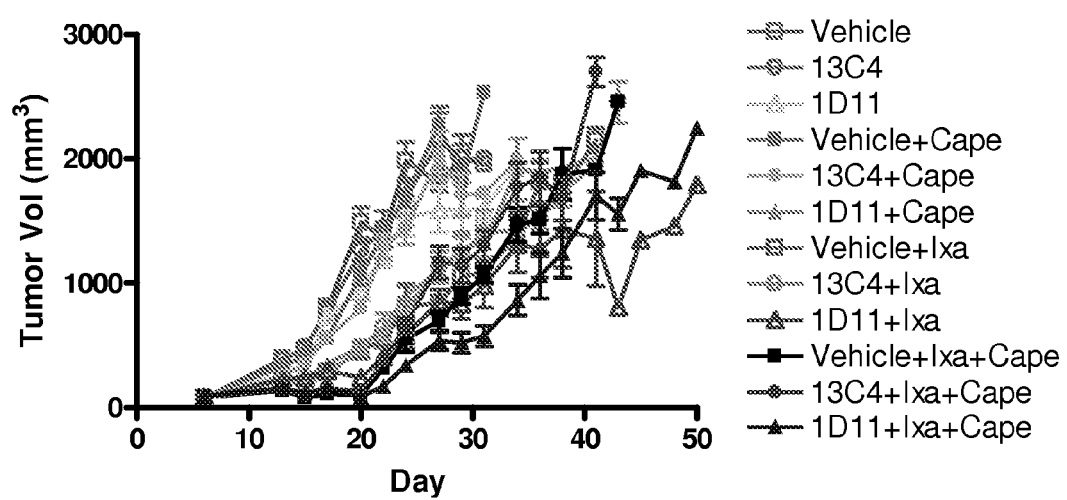
FIG. 1 shows mean primary tumor volumes. Inhibition of tumor growth was observed in the capecitabine, ixabepilone and capecitabine+ixabepilone cohorts compared to the antibody only cohort.

1D11 described herein represents an anti-TGFβ monoclonal antibody.

DETAILED DESCRIPTION OF THE INVENTION

The invention relates to compositions and methods for treating a breast cancer. Specifically, the invention relates to administering a TGFβ antagonist in combination with one or more chemotherapy agents to treat a breast cancer. The use of TGFβ antagonist in combination with one or more chemotherapy agents enhances the efficacy of the one or more chemotherapy agents to treat a breast cancer.

The chemotherapy agents of the invention include, but are not limited to, capecitabine, ixabepilone, or a combination thereof.

In one embodiment, provided herein is a method for enhancing the efficacy of a chemotherapy to treat a breast cancer in a subject, the method comprising: administering to said subject a therapeutically effective amount of a TGFβ antagonist in combination with capecitabine and ixabepilone, wherein the administration of said TGFβ antagonist enhances the efficacy of capecitabine and ixabepilone to treat said breast cancer.

In another embodiment, provided herein is a method for inhibiting a breast cancer associated tumor growth in a subject, the method comprising: administering to said subject a therapeutically effective amount of a TGFβ antagonist in combination with capecitabine and ixabepilone, wherein the administration of said TGFβ antagonist enhances the efficacy of capecitabine and ixabepilone to inhibit said breast cancer associated tumor growth.

The inventors of the instant application surprisingly and unexpectedly found that the neutralization of TGFβ in combination with one or more chemotherapy agents enhances the efficacy of the one or more chemotherapy agents to treat a breast cancer. For example, the use of TGFβ antagonist in combination with capecitabine and ixabepilone surprisingly and unexpectedly enhances the efficacy of capecitabine and ixabepilone to treat a breast cancer.

As used herein, "TGFβ" refers to all isoforms of TGFβ. There are currently 5 known isoforms of TGFβ (1-5), all of which are homologous (60-80% identity) and all of which form homodimers of about 25 kD, and act upon common TGFβ cellular receptors (Types I, II, and III). The genetic and molecular biology of TGFβ is well known in the art (see, for example, Roberts, 1998, Miner. Electrolyte and Metab., 24(2-3):111-119; Wrana, 1998, Miner. Electrolyte and Metab., 24(2-3):120-130.)

As used herein, a "TGFβ antagonist" is any molecule that is able to decrease the amount or activity of TGFβ, either within a cell or within a physiological system. Preferably, the TGFβ antagonist acts to decrease the amount or activity of a TGFβ 1, 2, or 3. For example, a TGFβ antagonist may be a molecule that inhibits expression of TGFβ at the level of transcription, translation, processing, or transport; it may affect the stability of TGFβ or conversion of the precursor molecule to the active, mature form; it may affect the neutralization of TGFβ or the ability of TGFβ to bind to one or more cellular receptors (e.g., Type I, II or III); or it may interfere with TGFβ signaling.

A variety of TGFβ antagonists and methods for their production are known in the art and many more are currently under development (see for example, Dennis et al., U.S. Pat. No. 5,821,227). The specific TGFβ antagonist employed is not a limiting feature; any effective TGFβ antagonist as defined herein may be useful in the methods and compositions of this invention. In one embodiment, the TGFβ antagonist is a TGFβ-1, TGFβ-2, or TGFβ-3 antagonist. In a particular embodiment, the TGFβ antagonist is a pan-specific anti-TGFβ antibody that binds to or neutralizes one or more isoforms of TGFβ.

The effects of TGFβ are mediated by the binding of active TGFβ to specific receptors present on cells, followed by transduction of signal to those cells. TGFβ antagonists are defined as agents that inhibit TGFβ signal transduction, including TGFβ antagonists which are known in the art. For example, agents that bind TGFβ and prevent TGFβ from binding to a TGFβ receptor will act as TGFβ antagonists.

Other non-limiting examples include blocking (neutralizing) antibodies specific for a human TGFβ (NAbs) such as those described by Dasch et al. (J. Immunol. (1989) 142: 1536) and Lucas et al. (J. Immunol. (1990) 145:1415), soluble TGFβ receptors, membrane-bound TGFβ receptors, protease inhibitors that inactivate a protease responsible for activating a precursor TGFβ into mature TGFβ, antibodies specific to TGFβ receptors (Types I, II or III) and which prevent TGFβ binding to the receptor, and combinations thereof.

Those skilled in the art recognize various ways in which an antibody derived from one species, for example a mouse, can be engineered in order to be therapeutically useful in a second species, for example a human. Certain of these techniques are briefly reviewed in Harris and Emery, TIBTECH 11:42-44, 1993.

TGFβ is generally secreted as a latent precursor consisting of TGFβ non-covalently associated with a protein designated latency-associated protein (LAP; reviewed in Harpel et al. (1992) Prog. Growth Factor Res. 4: 321). A DNA encoding a 278 amino acid peptide corresponding to pre-pro-TGFβ, terminating just prior to the mature form of TGFβ and containing a Cys33 to Ser33 substitution has been expressed (Derynck et al. (1985) Nature 316: 701), and found to bind TGFβ and render it latent.

Soluble forms of TGFβ receptors will also bind TGFβ and prevent binding to membrane-associated TGFβ receptors. TGFβ receptors are described by Wang et al. (Cell (1991) 67: 797) and Lin et al. (Cell (1992) 68: 775). Soluble forms of TGFβ receptors may be prepared by methods that are known in the art. For example, deletion mutants lacking the transmembrane domain of a TGFβ receptor can be prepared, which will express a soluble TGFβ binding protein. Miyazono et al. (Adv. Immunol. (1994) 55: 181) have reviewed TGFβ receptors Other types of TGFβ antagonists are also known in the art. For example, Yamaguchi et al. (Nature (1990) 346: 281) discuss decorin, a small chondroitin-dermatan sulphate proteoglycan that binds TGFβ and modulates the activity of this growth factor. Ohtsuki and Massague (Mol. Cell. Biol. 12:261-265, 1992) disclose protein kinase inhibitors that block certain biological activities of TGFβ. T. cruzi produces a cysteine protease (cruzain or cruzipain; Eakin et al. (1992) J. Biol. Chem. 267: 7411) which converts inactive TGFβ precursor into active, mature TGFβ. The design and use of protease inhibitors as drugs is well known in the art (Design of Enzyme Inhibitors as Drugs; Sandier and Smith, eds; 1989, Oxford University Press; Proteinase Inhibitors Medical and Biological Aspects; Katunuma, Umezawa and Holzer, eds., 1983, Springer-Verlag); thus, inhibitors of cruzain can be prepared and will be useful as TGFβ antagonists.

Still other TGFβ antagonists and methods for their production are well known in the art, with many more currently under development. The specific TGFβ antagonist employed is not a limiting feature, as any effective TGFβ antagonist may be useful in the methods of this invention. Examples of such antagonists include monoclonal and polyclonal antibodies directed against one or more isoforms of TGFβ (U.S. Pat. No. 5,571,714), TGFβ receptors, fragments thereof, derivatives thereof and antibodies directed against TGFβ receptors (U.S. Pat. Nos. 5,693,607, 6,008,011, 6,001,969 and 6,010,872); latency associated peptide (WO 91/08291), large latent TGFβ (WO 94/09812), fetuin (U.S. Pat. No. 5,821,227), decorin and other proteoglycans such as biglycan, fibromodulin, lumican and endoglin (U.S. Pat. Nos. 5,583,103, 5,654,270, 5,705,609, 5,726,149, 5,824,655, 5,830,847, and 6,015,693).

Further examples of such antagonists include somatostatin (PCT patent application WO 98/08529), mannose-6-phosphate or mannose-1-phosphate (U.S. Pat. No. 5,520, 926), prolactin (PCT patent application WO 97/40848), insulin-like growth factor II (PCT patent application WO 98/17304), IP-10 (PCT patent application WO97/00691), arg-gly-asp containing peptides (U.S. Pat. No. 5,958,411 and PCT patent application WO 93/10808 and), extracts of plants, fungi and bacteria (European patent application 813875, Japanese patent application 8119984 and U.S. Pat. No. 5,693,610), antisense oligonucleotides (U.S. Pat. Nos. 5,683,988, 5,772,995, 5,821,234 and 5,869,462 and PCT patent application WO 94/25588), and a host of other proteins involved in TGFβ signaling, including SMADs and MADs (U.S. Pat. Nos. 5,834,248, 5,807,708 and 5,948,639) and Ski and Sno (G. Vogel, Science, 286:665 (1999) and Stroschein et al., Science, 286:771-74 (1999)) and fragments and derivatives of any of the above molecules that retain the ability to inhibit the activity of TGFβ.

TGFβ receptors and TGFβ-binding fragments of TGFβ receptors, especially soluble fragments are useful TGFβ antagonists in the methods of the present invention. TGFβ receptors and the nucleic acids encoding them are well known in the art. The human nucleic acid sequence encoding TGFβ type 1 receptor is disclosed, for example, in GenBank accession number L15436 and in U.S. Pat. No. 5,538,892 of Donahoe et al. The human nucleic acid sequence of TGFβ type 2 receptor is publicly available, for example, under GenBank accession numbers AW236001; AI35790; AI279872; AI074706; and AA808255. The human nucleic acid sequence of TGFβ type 3 receptor is also publicly available, for example, under GenBank accession, numbers NM 003243; AI887852; AI817295; and AI681599.

In a preferred embodiment, the TGFβ antagonist is an antibody that blocks TGFβ binding to its receptor, or fragments thereof such as Fab, Fab', F(ab')$_2$ fragments, Fv fragments, single chain antibodies and other forms of "antibodies" that retain the ability to bind to TGFβ. In one embodiment, the antibody is a pan-specific anti-TGFβ antibody. In one example, the pan-specific anti-TGFβ antibody binds to and neutralizes one or more isoforms of TGFβ. In another example, the pan-specific anti-TGFβ antibody blocks or inhibits the binding of a protein to one or more isoforms of TGFβ.

In one embodiment, the antibody is a monoclonal antibody. In another embodiment, the antibody is a human antibody. In another embodiment, the antibody is a humanized antibody. In another embodiment, the antibody is a chimeric antibody. In a particular embodiment, the antibody is a humanized form of the murine monoclonal antibody 1D11, deposited under ATCC number HB9849. In another particular embodiment, the antibody is an anti-TGFβ antibody described in U.S. patent application Ser. No. 11/350,906, filed Feb. 8, 2006 (U.S. 2006/0251658), which is incorporated by reference herein in its entirety. In another particular embodiment, the antibody comprises one or more CDRs of 1D11 described in U.S. patent application Ser. No. 11/350,906.

As used herein, the term "antibody" includes intact immunoglobulin molecules comprising 4 polypeptide chains, two heavy (H) chains and two light (L) chains inter-connected by disulfide bonds. Each heavy chain is comprised of a heavy chain variable region (abbreviated herein as VH) and a heavy chain constant region. The heavy chain constant region contains three domains, CH1, CH2 and CH3. Each light chain is comprised of a light chain variable region (abbreviated herein as VL) and a light chain constant region. The light chains of antibodies from any vertebrate species can be assigned to one of two clearly distinct types, called kappa (κ) and lambda (λ), based on the amino acid sequences of their constant domains. The variable regions of kappa light chains are referred to herein as VK. The expression of VL, as used herein, is intended to include both the variable regions from kappa-type light chains (VK) and from lambda-type light chains. The light chain constant region is comprised of one domain, CL. The VH and VL regions include regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1-CDR1-FR2-CDR2-FR3-CDR3-FR4. "CDRH1" refers to the first CDR region in an antibody heavy chain, "CDRH2" refers to the second CDR region in an antibody heavy chain, and "CDRH3" refers to the third CDR region in an antibody heavy chain. "CDRL1" refers to the first CDR region in an antibody light chain, "CDRL2" refers to the second CDR region in an antibody light chain, and "CDRL3" refers to the third CDR region in an antibody light chain.

Depending on the amino acid sequence of the constant domain of their heavy chains, antibodies can be assigned to different classes. There are 5 major classes of intact antibodies: IgA, IgD, IgE, IgG, and IgM. Several of these may be further divided into subclasses (isotypes), e.g., IgG1, IgG2, IgG3, IgG4, IgA, and IgA2. The heavy-chain constant domains that correspond to the different classes of antibodies are called alpha (α), delta (Δ), epsilon (ε), gamma (γ), and mu (μ), respectively. The subunit structures and three-dimensional configurations of different classes of immunoglobulins are well known. The present invention includes antibodies of any of the aforementioned classes or subclasses (isotypes).

The term "antibody" as used herein is also intended to encompass intact antibodies, functional fragments which bind antigen, and variants thereof which bind antigen, including antibody mimetics or comprising portions of antibodies that mimic the structure and/or function of an antibody or specified fragment or portion thereof; each containing at least one CDR. Antibodies of the invention include antibody fragments or variants having one, two, three, four, five, six or more CDR regions.

Antibody fragments which are embraced by the present invention include Fab (e.g., by papain digestion), Fab', F(ab')$_2$, facb (e.g., by plasmin digestion), pFc' (e.g., by pepsin or plasmin digestion), Fd (e.g., by pepsin digestion, partial reduction and reaggregation), sVds, and Fv or scFv (e.g., by molecular biology techniques). Antibody fragments are also intended to include domain deleted antibodies, diabodies, triabodies, linear antibodies, single-chain antibody molecules (including camelized antibodies), and multispecific antibodies formed from antibody fragments.

The term "antibody," as used herein, also includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species (e.g., mouse or rat) or belonging to another antibody class or subclass, as well as fragments of such antibodies, so long as they exhibit the desired biological activity. Thus, the present invention includes, for example, chimeric antibodies comprising a chimeric heavy chain and/or a chimeric light chain. The chimeric heavy chain may comprise any of the heavy chain variable (VH) regions described herein or mutants or variants thereof fused to a heavy chain constant region of a non-human antibody. The chimeric light chain may comprise any of the light chain variable (VL) regions described herein or mutants or variants thereof fused to a light chain constant region of a non-human antibody.

Antibodies of the invention also include "humanized antibodies", which are antibody molecules having one or more complementarity determining regions (CDRs) from a non-human species and framework regions from a human immunoglobulin molecule. Often, framework residues in the human framework regions will be substituted with the corresponding residue from the CDR donor antibody to alter, or improve, antigen binding. These framework substitutions are identified standard techniques such as by modeling of the interactions of the CDR and framework residues to identify framework residues important for antigen binding and sequence comparison to identify unusual framework residues at particular positions. Antibodies can be humanized using a variety of techniques including CDR-grafting, veneering or resurfacing, and chain shuffling.

The term "human antibody," as used herein, includes antibodies having variable and constant regions corresponding to human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs. The human antibody can have at least one position replaced with an amino acid residue, e.g., an activity enhancing amino acid residue which is not encoded by the human germline immunoglobulin sequence. However, the term "human antibody," as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences.

The term "monoclonal antibody," as used herein, refers to an antibody obtained from a population of substantially homogeneous antibodies, e.g., the individual antibodies comprising the population are substantially identical except for possible naturally occurring mutations or minor post-translational variations that may be present. Monoclonal antibodies are highly specific, being directed against a single antigenic site (also known as determinant or epitope). Furthermore, in contrast to conventional (polyclonal) antibody preparations which typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

Antibodies also include polypeptides with amino acid sequences substantially similar to the amino acid sequence of the variable or hypervariable regions of the heavy and/or light chain. Substantially the same amino acid sequence is defined herein as a sequence with at least 70%, 75%, 80%, 85%, 90%, 95%, or 99% identity to a compared amino acid sequence, as determined by the FASTA search method in accordance with Pearson and Lipman, *Proc. Natl. Acad. Sci. USA* 85:2444-2448 (1988).

Antibodies of the invention include those which are identical to those described herein except with one or more conservative amino acid substitutions. Conservative amino acid substitution is defined as a change in the amino acid composition by way of changing one or two amino acids of a peptide, polypeptide or protein, or fragment thereof. The substitution is of amino acids with generally similar properties (e.g., acidic, basic, aromatic, size, positively or negatively charged, polarity, non-polarity) such that the substitutions do not substantially alter peptide, polypeptide or protein characteristics (e.g., charge, isoelectric point, affinity, avidity, conformation, solubility) or activity. Typical substitutions that may be performed for such conservative amino acid substitution may be among the groups of amino acids as follows: glycine (G), alanine (A), valine (V), leucine (L) and isoleucine (I); aspartic acid (D) and glutamic acid (E); alanine (A), serine (S) and threonine (T); histidine (H), lysine (K) and arginine (R); asparagine (N) and glutamine (Q); phenylalanine (F), tyrosine (Y) and tryptophan (W).

Conservative amino acid substitutions can be made in the CDR or framework regions, e.g., regions flanking the hypervariable regions primarily responsible for the selective and/or specific binding characteristics of the molecule, as well as other parts of the molecule, e.g., variable heavy chain cassette.

Antibodies of the present invention also include those having their affinity increased or altered by direct mutation, affinity maturation, phage display, or chain shuffling. Affinity and specificity can be modified or improved by mutating CDR and/or framework residues and screening for antigen binding sites having the desired characteristics. One way is to randomize individual residues or combinations of residues so that in a population of, otherwise identical antigen binding sites, subsets of from two to twenty amino acids are found at particular positions. Alternatively, mutations can be induced over a range of residues by error using PCR methods. In another example, phage display vectors containing heavy and light chain variable region genes can be propagated in mutated strains of *E. coli*.

Antibodies prepared by chain shuffling, include those where the heavy or light chain are randomly paired with other heavy or light chains described herein. Thus, the antibodies of the invention include any combination of heavy and light chains (either full length or portions thereof).

The antibodies of the present invention are specific for TGFβ. Antibody specificity refers to selective recognition of the antibody for a particular epitope of an antigen. The antibodies may exhibit both species and molecule selectivity, or may be selective with respect to molecule only and bind to TGFβ of more than one species. The antibodies of the invention may bind to human, murine, rat, dog and/or rabbit TGFβ. In one embodiment, the antibody binds to human TGFβ. Whether an antibody binds specifically to a TGFβ can be determined, e.g., by a binding assay such as an ELISA, employing a panel of antigens.

Specificity of the antibodies can be determined based on affinity and/or avidity. Affinity, represented by the equilibrium constant for the dissociation of an antigen with an antibody ($K_d$), measures the binding strength between an antigenic determinant and an antibody-binding site. Avidity is the measure of the strength of binding between an antibody with its antigen. Avidity is related to both the affinity between an epitope with its antigen binding site on the antibody, and the valence of the antibody, which refers to the number of antigen binding sites of a particular epitope. Antibodies typically bind with a dissociation constant ($K_d$) of about $10^{-5}$ to about $10^{-11}$ liters/mol (e.g., $K_D$<100 nM). Any $K_d$ less than about $10^{-4}$ liters/mol is generally considered to indicate nonspecific binding. The lesser the value of the $K_d$, the stronger the binding strength between an antigenic determinant and the antibody binding site.

The antibodies of the invention bind to TGFβ with a Kd of preferably about $1\times10^{-8}$ $M^{-1}$ or less, more preferably about $1\times10^{-9}$ $M^{-1}$ or less, more preferably about $1\times10^{-10}$ $M^{-1}$ or less, and most preferably about $1\times10^{-11}$ $M^{-1}$ or less.

Antibodies of the present invention can be monospecific, bispecific or multispecific. Monospecific antibodies bind to only one antigen. Bispecific antibodies (BsAbs) are antibodies that have two different antigen-binding specificities or sites. Multispecific antibodies have more than two different antigen-binding specificities or sites. Where an antibody has more than one specificity, the recognized epitopes can be associated with a single antigen or with more than one antigen.

In another aspect of the invention, the antibody is conjugated to another moiety, either directly or indirectly. The conjugation may be chemical or biosynthetic. Other moieties which can be conjugated to the antibodies include toxins, anti-tumor agents, detectable labels, target moieties and reporter moieties. Suitable toxins are described herein.

In one embodiment, one or more chemotherapy agents of the invention are operably linked to the antibody. For example, capecitabine, ixabepilone, or both may be conjugated to the anti-TGFβ antibody.

Antibodies which are conjugated to detectable labels can be used, for example, to diagnose a disease, to aid in prognosis and to locate tumor cells, in vivo or in vitro. The detectable label produces a measurable signal which is detectable by external means. Detectable labels include an enzyme, a chromophore, a radioisotope, or a substance that emits light by fluorescence, phosphorescence or chemiluminescence. Suitable enzymes include horseradish peroxidase, alkaline phosphatase, β-galactosidase, and acetylcholinesterase. Chromophores include dyes which absorb light in the ultraviolet or visible region, and can be substrates or degradation products of enzyme catalyzed reactions. Suitable fluorescent materials include umbelliferone, fluorescein, fluorescein isothiocyanate, rhodamine, dichlorotriazinylamine fluorescein, dansyl chloride or phycoerythrin. Suitable chemiluminescence materials include luminol, luciferase, luciferin, and aequorin. Suitable radioactive materials include 125I, 131I, 35S, and 3H.

Target moieties are first members of binding pairs. Anti-tumor agents, for example, may be conjugated to second members of such pairs and are thereby directed to the site where the antigen-binding protein is bound. A common example of such a binding pair is avidin and biotin. Biotin may be conjugated to an antibody of the invention, thereby providing a target for an anti-tumor agent or other moiety which is conjugated to avidin or streptavidin. Alternatively, biotin or another such moiety is linked to an antigen-binding protein of the invention and used as a reporter, for example, a detectable label is conjugated to avidin or streptavidin.

The present invention also includes nucleic acid molecules that encode an anti-TGFβ antibody or portion thereof. Nucleic acids may encode an antibody heavy chain, comprising any one of the VH regions or a portion thereof, or any one of the VH CDRs, including any variants thereof, as disclosed herein. The invention also includes nucleic acid molecules that encode an antibody light chain comprising any one of the VL regions or a portion thereof or any one of the VL CDRs, including any variants thereof as disclosed herein. In certain embodiments, the nucleic acid encodes both a heavy and light chain, or portions thereof.

The invention also includes recombinant vectors comprising any of the nucleic acid molecules described herein. The vector may comprise a nucleic acid encoding only one antibody chain or a portion thereof (e.g., the heavy or light chain) or a nucleic acid encoding both antibody chains or portions thereof.

Exemplary vectors include plasmids, phagemids, cosmids, viruses and phage nucleic acids or other nucleic acid molecules that are capable of replication in a prokaryotic or eukaryotic host. The vectors typically contain a marker to provide a phenotypic trait for selection of transformed hosts such as conferring resistance to antibiotics such as ampicillin or neomycin The vector may be an expression vector, wherein the nucleic acid encoding the antibody is operably linked to an expression control sequence. Typical expression vectors contain transcription and translation terminators, initiation sequences, and promoters useful for regulation of the expression of the nucleic acid molecules of the invention. The vectors may also contain genetic expression cassettes containing an independent terminator sequence, sequences permitting replication of the vector in both eukaryotes and prokaryotes, i.e., shuttle vectors and selection markers for both prokaryotic and eukaryotic systems. When the vector contains nucleic acids encoding both a heavy and light chain or portions thereof, the nucleic acid encoding the heavy chain may be under the same or a separate promoter. The separate promoters may be identical or may be different types of promoters.

Suitable promoters include constitutive promoters and inducible promoters. Representative expression control sequences/promoters include the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., PhoS, the promoters of the yeast alpha mating factors, promoters derived from the human cytomegalovirus, metallothionine promoter, murine mammary tumor virus promoter, Rous sarcoma virus promoter, polyhedrin promoter and promoters derived from polyoma, adenovirus, retrovirus, and simian virus, e.g., the early and late promoters of SV40.

The invention also includes non-human hosts such as cells or organisms containing a nucleic acid molecule or a vector of the invention. By "host" it is meant a non-human unicellular or multicellular organism or a "host cell", which refers to a cell or population of cells into which a nucleic acid molecule or vector of the invention is introduced. "A population of host cells" refers to a group of cultured cells into which a nucleic acid molecule or vector of the present invention can be introduced and expressed. The host contain a nucleic acid or vector encoding only one chain or portion thereof (e.g., the heavy or light chain); or it may contain a nucleic acid or vector encoding both chains or portions thereof, either an the same or separate nucleic acids and/or vectors.

A host of the present invention may be prokaryotic or eukaryotic. Suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas*, *Bacillus*, such as *Bacillus subtilis*, and *Streptomyces*. Suitable eukaryotic cells include yeast and other fungi, insect cells, plant cells, human cells, and animal cells, including mammalian cells, such as hybridoma lines, COS cells, NS0 cells and CHO cells.

The invention also includes methods of producing an antibody of the present invention, which entails culturing a host cell expressing one or more nucleic acid sequences encoding an antibody of the present invention, and recovering the antibody from the culture medium. In certain embodiments, the antibody is purified by separating it from the culture medium. Antibodies comprising more than one chain can be produced by expressing each chain together in the same host; or as separate chains, which are assembled before or after recovery from the culture medium.

Methods for making other TGFβ antagonists are well known in the art, as described above.

Capecitabine was generally disclosed in U.S. Pat. No. 4,966,891 and specifically disclosed in U.S. Pat. No. 5,472,949. In pharmaceutical compositions, it is marketed under the brand name XELODA by Roche Laboratories Inc. (USA). Various synthetic processes leading to capecitabine are known in the prior art, for example, methods for making capecitabine are described in U.S. Patent Application Publication 20080300399, which is incorporated by reference herein in its entirety.

Methods for making ixabepilone are also well known in the art. For example, enteric coated bead comprising ixabepilone, and preparation and administration thereof is described in U.S. Patent Application Publication 20060153917, which is incorporated by reference herein in its entirety.

In another embodiment, provided herein is a pharmaceutical composition to treat a breast cancer in a subject, comprising: a therapeutically effective amount of a TGFβ antagonist, capecitabine and/or ixabepilone, wherein said TGFβ antagonist is present in an amount effective to enhance the efficacy of capecitabine and/or ixabepilone to treat said breast cancer. In some embodiments, a first pharmaceutical composition comprises a TGFβ antagonist, a second pharmaceutical composition comprises capecitabine, and a third pharmaceutical composition comprises ixabepilone. These individual and separate compositions may be administered independently or together.

The invention also provides a pharmaceutical composition comprising the antibody, nucleic acid, vector, host cell, or chemotherapy agents of this invention and one or more pharmaceutically acceptable carriers. "Pharmaceutically acceptable carriers" include any excipient which is nontoxic to the cell or mammal being exposed thereto at the dosages and concentrations employed. The pharmaceutical composition may include one or additional therapeutic agents.

Pharmaceutically acceptable carriers include solvents, dispersion media, buffers, coatings, antibacterial and antifungal agents, wetting agents, preservatives, buggers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

The pharmaceutical compositions of the invention may be formulated in a variety of ways, including for example, liquid, semi-solid and solid dosage forms, such as liquid solutions (e.g., injectable and infusible solutions), dispersions or suspensions, tablets, pills, powders, liposomes and suppositories. In some embodiments, the compositions are in the form of injectable or infusible solutions. The composition is in a form suitable for oral, intravenous, intraarterial, intramuscular, subcutaneous, parenteral, transmucosal, transdermal, or topical administration. The composition may be formulated as an immediate, controlled, extended or delayed release composition.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

In some embodiments, the composition includes isotonic agents, for example, sugars, polyalcohols, such as mannitol, sorbitol, or sodium chloride. Prolonged absorption of the injectable compositions can be brought about by including in the composition an agent which delays absorption, for example, aluminum monostearate and gelatin.

Sterile injectable solutions can be prepared by incorporating the molecule, by itself or in combination with other active agents, in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, one method of preparation is vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in US Appl. Publ. No. 2002/0102208 A1, which is incorporated herein by reference in its entirety. Such articles of manufacture will preferably have labels or package inserts indicating that the associated compositions are useful for treating a subject suffering from, or predisposed to autoimmune or neoplastic disorders.

Effective doses of the compositions of the present invention, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

The invention further provides a kit comprising a therapeutically effective amount of a TGFβ antagonist, capecitabine, ixabepilone, or combination thereof.

The invention further provides methods of treating a disease or condition, comprising administering to a mammal in need thereof a therapeutically effective amount of a TGFβ antagonist, capecitabine, ixabepilone, or combination thereof.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

Cancers/tumors which may be treated by the invention include any cancer or tumor. Examples of cancers/tumors which may be treated include, but are not limited to, breast cancer (including HER2+ and metastatic), a cancer treated by capecitabine, ixabepilone, or both, or a cancer associated with the TGFβ mediated signaling.

Methods of treating cancer include, but are not limited to, e.g., inhibiting angiogenesis in the tumor, inhibiting tumor growth, inhibiting tumor migration, inhibiting proliferation or inhibiting invasion of tumor cells.

Cancers that express or overexpress or are associated with the expression or overexpression of TGFβ may be treated by the invention. However, cancer to be treated by the combination therapy herein may be any cancer, not simply those that express or overexpress TGFβ.

Cancers to be treated include primary tumors and secondary or metastatic tumors (including those metastasized from lung, breast, or prostate), as well as recurrent or refractory tumors. Recurrent tumors encompass tumors that appear to be inhibited by treatment with such agents, but recur up to five years, sometimes up to ten years or longer after treatment is discontinued. Refractory tumors are tumors that have failed to respond or are resistant to treatment with one or more conventional therapies for the particular tumor type. Refractory tumors include those that are hormone-refractory (e.g., androgen-independent prostate cancer; or hormone-refractory breast cancer, such as breast cancer that is refractory to tamoxifen); those that are refractory to treatment with one or more chemotherapeutic agents; those that are refractory to radiation; and those that are refractory to combinations of chemotherapy and radiation, chemotherapy and hormone therapy, or hormone therapy and radiation Therapy may be "first-line", i.e., as an initial treatment in patients who have had no prior anti-cancer treatments, either alone or in combination with other treatments; or "second-line", as a treatment in patients who have had one prior anti-cancer treatment regimen, either alone or in combination with other treatments; or as "third-line", "fourth-line", etc. treatments, either alone or in combination with other treatments.

Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of tumor.

Cancers that may be treated include tumors that are not vascularized, or not yet substantially vascularized, as well as vascularized tumors. The cancers may be comprised of non-solid tumors (such as leukemias and lymphomas) or may be solid tumors. Types of cancers to be treated with the antibodies of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are included.

More than one TGFβ antagonist may be administered, either incorporated into the same composition or administered as separate compositions.

The TGFβ antagonist may be administered alone, or in combination with one or more therapeutically effective agents (e.g., capecitabine, ixabepilone, or both) or treatments. The other therapeutically effective agent may be conjugated to the TGFβ antagonist, incorporated into the same composition as the TGFβ antagonist, or may be administered as a separate composition. The other therapeutically agent or treatment may be administered prior to, during and/or after the administration of the TGFβ antagonist.

In one embodiment, TGFβ antagonist is co-administered with capecitabine, ixabepilone, or a combination thereof. In another embodiment, TGFβ antagonist is administered independently from the administration of capecitabine, ixabepilone, or a combination thereof. In one embodiment, TGFβ antagonist is administered first, followed by the administration of capecitabine, ixabepilone, or a combination thereof. In another embodiment, capecitabine, ixabepilone, or a combination thereof is administered first, followed by the administration of TGFβ antagonist.

Other therapeutically effective agents/treatments include surgery, anti-neoplastics (including chemotherapeutic agents and radiation), anti-angiogenesis agents, antibodies to other targets, small molecules, photodynamic therapy, immunotherapy, cytotoxic agents, cytokines, chemokines, growth inhibitory agents, anti-hormonal agents, kinase inhibitors, cardioprotectants, immunostimulatory agents, immunosuppressive agents, agents that promote proliferation of hematological cells, and protein tyrosine kinase (PTK) inhibitors.

A chemotherapeutic agent may be administered as a prodrug. The term "prodrug" refers to a precursor or derivative form of a pharmaceutically active substance that is less cytotoxic to tumor cells compared to the parent drug and is capable of being enzymatically activated or converted into the more active parent form. The prodrugs that may find use with the compositions and methods as provided herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies and Fc fusions of the compositions and methods as provided herein include but are not limited to any of the aforementioned chemotherapeutic agents.

The administration of the TGFβ antagonist with other agents (e.g., capecitabine, ixabepilone, or both) and/or treatments may occur simultaneously, or separately, via the same or different route, at the same or different times. Dosage regimens may be adjusted to provide the optimum desired response (e.g., a therapeutic or prophylactic response).

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

The composition of the invention may be administered only once, or it may be administered multiple times. For multiple dosages, the composition may be, for example, administered three times a day, twice a day, once a day, once every two days, twice a week, weekly, once every two weeks, or monthly.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets). Administration to a host may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

The composition of the invention (e.g., TGFβ antagonist) may be administered parenterally (e.g., intravenous, subcutaneous, intraperitoneal, intramuscular). Further, the composition of the invention may be administered by intravenous infusion or injection. The composition of the invention may be administered by intramuscular or subcutaneous injection. In some embodiments, the composition of the invention (e.g., capecitabine and/or ixabepilone) may be administered orally. As used herein, a "composition" refers to any composition that contains a pharmaceutically effective amount of one or more active ingredients (e.g., a TGFβ antagonist, capecitabine, ixabepilone, or a combination thereof).

The methods of treatment described herein can be used to treat any suitable mammal, including primates, such as monkeys and humans, horses, cows, cats, dogs, rabbits, and rodents such as rats and mice. In one embodiment, the mammal to be treated is human.

All patents and literature references cited in the present specification are hereby incorporated by reference in their entirety.

EXAMPLES

Example 1

Study 1: The Effects of 1D11, Ixabepilone, Capecitabine and Combinations of these Therapeutics on Primary Tumor Growth and Metastases in a Syngeneic Triple-Negative Breast Cancer Model (4T1)

Clinically, the combination of the chemotherapeutics ixabepilone and capecitabine has been shown to be effective in the treatment of metastatic or locally advanced triple-negative breast cancer (TNBC) that has been resistant to taxanes. This pre-clinical study was conducted to: (1) determine the effects of 1D11, ixabepilone and capecitabine as single agents on the growth of subcutaneous 4T1 tumors and subsequent metastases to the lungs, (2) determine if combinatorial therapies with these agents result in additive or synergistic effects on the efficacy of individual agents, and (3) provide insight into potential safety/toxicity issues with these combinatorial therapies.

Experimental Methods:

TABLE 1

Study Outline

| Group # | Treatment Groups | Animals per group |
|---|---|---|
| 1 | Antibody Vehicle | 10 |
| 2 | 13C4 10 mg/kg | 10 |
| 3 | 1D11 10 mg/kg | 10 |
| 4 | Antibody Vehicle + Capecitabine | 10 |
| 5 | 13C4 + Capecitabine | 10 |
| 6 | 1D11 + Capecitabine | 10 |
| 7 | Antibody Vehicle + Ixabepilone | 10 |
| 8 | 13C4 + Ixabepilone | 10 |
| 9 | 1D11 + Ixabepilone | 10 |
| 10 | Antibody Vehicle + Capecitabine + Ixabepilone | 10 |
| 11 | 13C4 + Capecitabine + Ixabepilone | 10 |
| 12 | 1D11 + Capecitabine + Ixabepilone | 10 |

Time points: Day 0: Investigators inject 50,000 4T1 cells + matrigel subcutaneously in the right flank Day 3: Investigators begin 2-3X/week tumor measurements Day 6: DCM Staff begin antibody dosing IP 3X/week DCM Staff begin ixabepilone dosing IV Q4Dx3 DCM Staff begin capecitabine dosing by oral gavage QDx14

Animals were sacrificed when the primary tumors reached a volume of 2000 mm$^3$ or prior to the study takedown if they presented with moribund conditions (lack of grooming, labored breathing, cachexia, anorexia, or lethargy). After sacrifice, the primary tumor was halved with one half embedded in OCT, and the other placed in zinc buffered formalin. The lungs and any other tissues bearing metastases were harvested and stored in zinc buffered formalin for enumeration of lung mets and IHC.

Tissues: Primary tumors in OCT and zinc buffered formalin, lungs harvested in zinc buffered formalin for assessment of metastasis and subsequent IHC.

On Day 0, 150 twelve week-old female BALB/c mice each received subcutaneous injections of 50,000 4T1 cells in Matrigel in the right flank. Tumor-bearing mice were routinely monitored and regular tumor measurements 2-3×/week were conducted beginning on Day 6. Tumor volume was determined using the following formula:

$$\text{Tumor Volume} = \text{Length} \times \text{Width}^2 \times 0.52$$

Six days after tumor cell injection, when tumor volumes averaged 80 mm$^3$, the animals were size-matched and divided into twelve treatment groups of ten mice each. Thirty mice with primary tumors that were either significantly larger that the average or were non-palpable (0 mm$^3$) were removed from the study. At this point investigators were blinded to treatment group designations and therapeutic administration was initiated. All mice received 10 mg/kg of either 1D11, 13C4 or antibody vehicle administered in 100 µl IP three times per week (Table 1). Specific cohorts of mice received additional treatments of ixabepilone (6 mg/kg in 200 l IV Q4D×3), capecitabine (360 mg/kg in 100 µl by oral gavage QD×14) or both.

Mice were sacrificed once primary tumor volumes reached 2000 mm$^3$ or greater or if the tumors became ulcerated >20% of the tumor's surface area, or if the animals presented with moribund conditions (lack of grooming, labored breathing, cachexia, anorexia or lethargy). Upon sacrifice, gross necropsies were performed and tumors, lungs and other tissues bearing metastases were harvested. A portion of the primary tumor was frozen in OCT for IHC of immunomarkers, and the remaining tumor and other tissues bearing metastases will be fixed zinc-formalin for paraffin embedding.

Results:

Study 09-3493 study mice received treatments of antibody vehicle, 13C4 or 1D11 three times a week for seven consecutive weeks. There was no difficulty with dosing the ixabepilone, capecitabine or antibody therapeutics; likely due to the use of BALB/c mice from Charles River in this study.

TABLE 2

Apparent treatment-related adverse events in Study.

| Group # | Mouse ID # | Status | Study day | Observations |
|---|---|---|---|---|
| Vehicle + Cape + Ixa | B7171 | found dead | 14 | Emaciated and hunched. No palpable primary tumor. Found dead in the evening following chemotherapeutic. |
| Vehicle + Cape + Ixa | B1741 | moribund | 20 | Emaciated and hunched. Displayed spasmodic muscle twitching. Sacrificed due to moribund state. |
| Vehicle + Cape + Ixa | B1793 | found dead | 17 | Emaciated and hunched. No palpable primary tumor. |
| Vehicle + Cape + Ixa | B1835 | moribund | 20 | Emaciated and hunched. Displayed spasmodic muscle twitching. Inability to use hind legs. Sacrificed due to moribund state. |
| 13C4 + Cape + Ixa | B1718 | found dead | 16 | Emaciated and hunched. No palpable primary tumor. |
| 13C4 + Cape + Ixa | B1765 | found dead | 18 | Emaciated and hunched. Small palpable primary tumor. No tissues taken. |
| 13C4 + Cape + Ixa | B1787 | found dead | 18 | Emaciated and hunched. Small palpable primary tumor. No tissues taken. |
| 13C4 + Cape + Ixa | B1804 | moribund | 17 | Emaciated and hunched. Inability to use hind legs. Sacrificed due to moribund state |
| 1D11 + Cape + Ixa | B1800 | found dead | 14 | Emaciated and hunched. No palpable primary tumor. Found dead in the evening following chemotherapeutic. |
| 1D11 + Cape + Ixa | B1808 | found dead | 18 | Emaciated and hunched. No palpable primary tumor. No tissues taken. |

Several mice on this study in the capecitabine+ixabepilone cohort were either found dead or needed to be sacrificed due to presentation of moribund conditions. These treatment-related toxicities are described in Table 1. The mice that required euthanasia were emaciated, scruffy, hunched and had difficulty breathing. Some mice in the groups treated with ixabepilone displayed some peripheral neuropathy; the mice had difficulty ambulating with their hind limbs. However, as observed in previous studies testing ixabepilone in this model, the neuropathy resolved following the last dose of chemotherapeutics. The addition of 1D11 to the chemotherapeutics did not increase or decrease the incidence of these toxicities.

Figure 2:
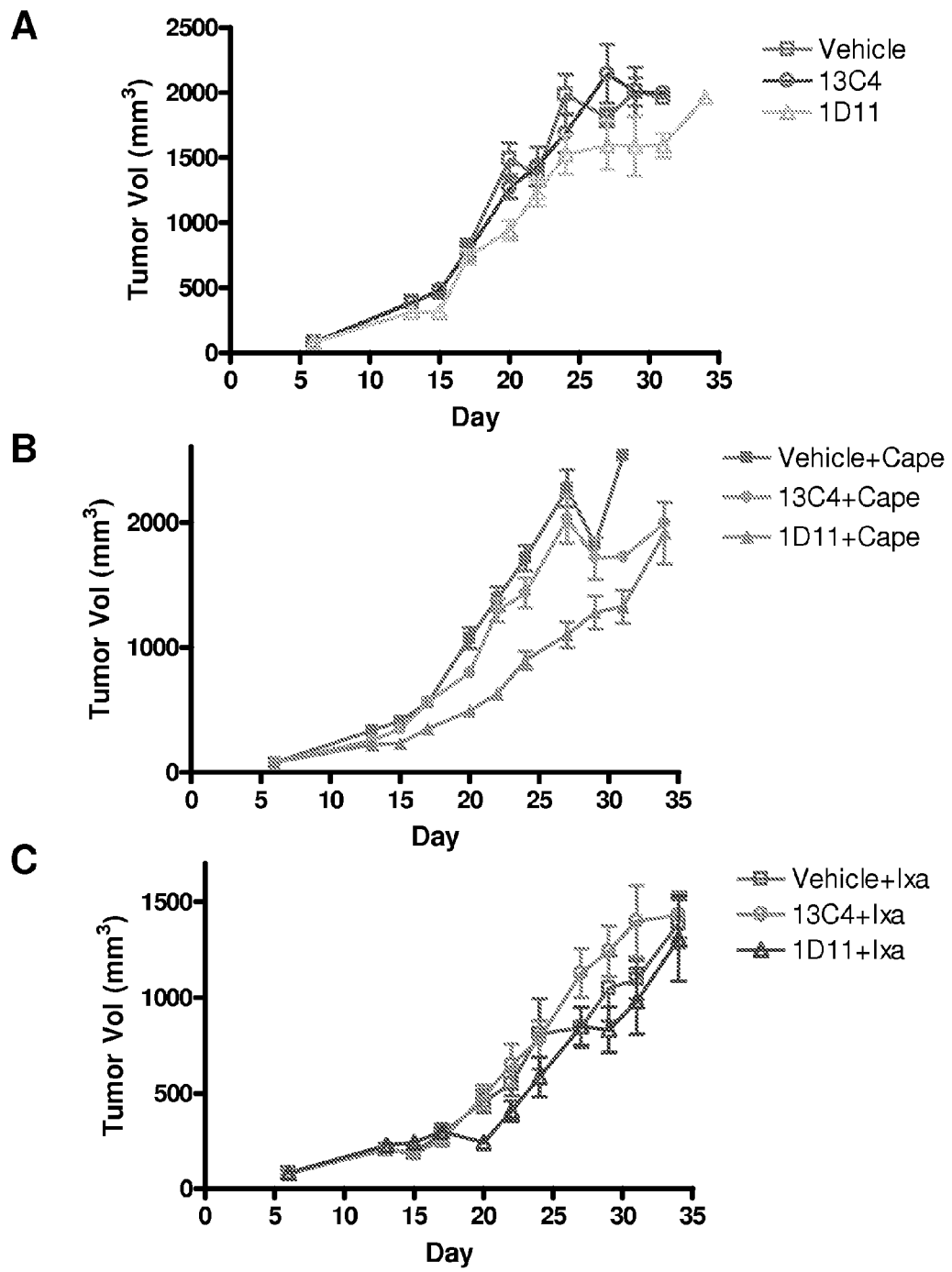
FIG. 2 shows that 1D11 as a single agent had relatively no effect on 4T1 tumor growth (A). 1D11 enhanced the efficacy of capecitabine (B) but not the efficacy of ixabepilone (C).

There were differential effects on tumor growth depending on the treatment provided (FIG. 1). As a single agent, 1D11 had no significant effect on the growth of SQ 4T1 tumors (FIG. 2A). As a monotherapy, ixabepilone was most efficacious at inhibiting 4T1 tumor growth compared to either antibody therapy or capecitabine, though capecitabine did inhibit tumor growth as well. The addition of 1D11 to capecitabine therapy resulted in enhanced efficacy over capecitabine alone or with 13C4 (FIG. 2B), however 1D11 did not enhance the efficacy of ixabepilone alone (FIG. 2C).

Figure 3:
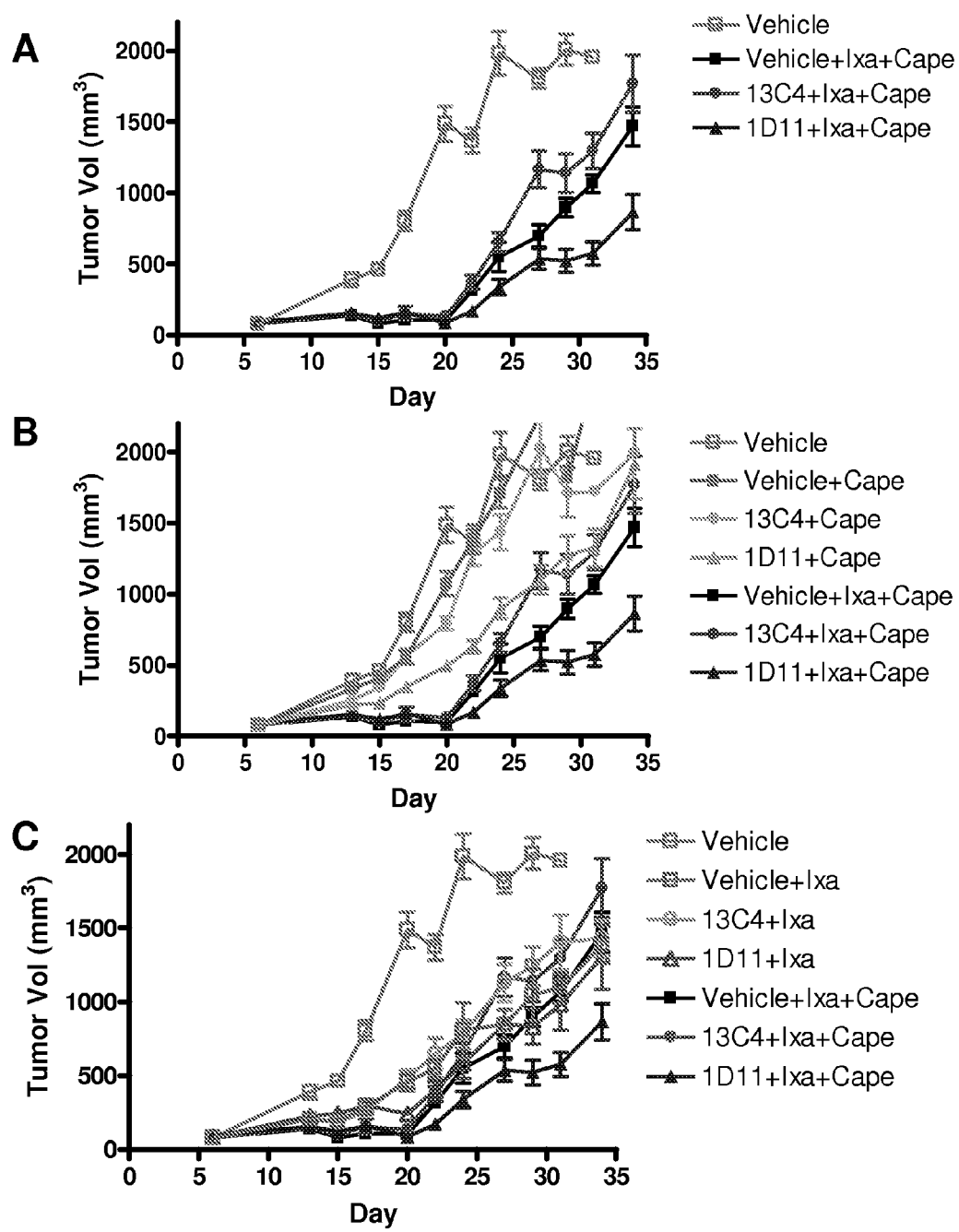
FIG. 3 shows that the addition of 1D11 enhanced the efficacy of the combinatorial therapy of capecitabine+ixabepilone in inhibiting 4T1 tumor growth (A). Capecitabine inhibited 4T1 tumor growth but was not as efficacious as ixabepilone, although 1D11 enhanced the efficacy of capecitabine, resulting in 4T1 tumor growth inhibition similar to that with ixabepilone alone (B). There was no significant advantage of the capecitabine+ixabepilone combination therapy over ixabepilone alone unless 1D11 was also included in the combinatorial therapy (C).
Figure 4:
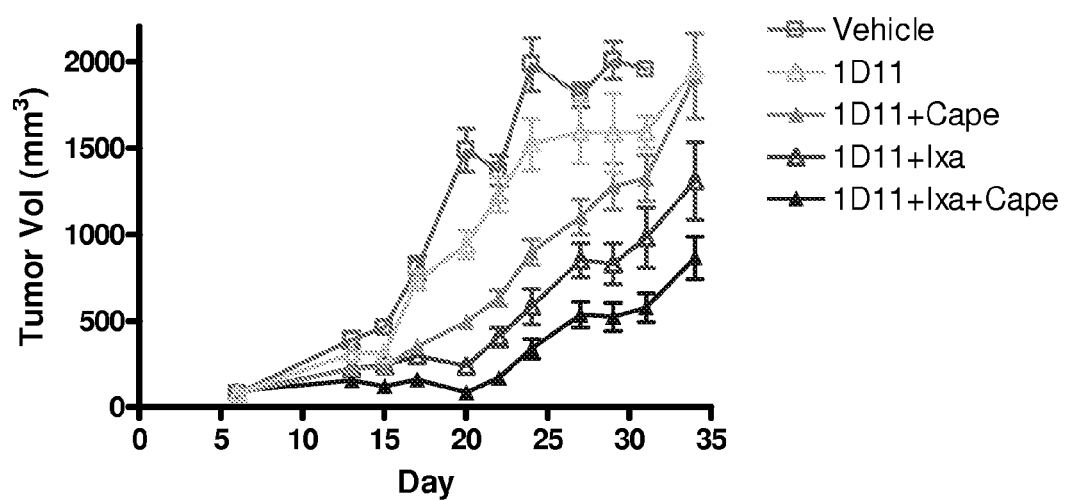
FIG. 4 shows an overview of the effects of 1D11 as a single agent or in combination of capecitabine and/or ixabepilone on 4T1 tumor growth. The most effective therapy is the triple combination of 1D11+capecitabine+ixabepilone.

The strongest inhibition of tumor growth was observed in mice receiving the combinatorial therapy of 1D11+capecitabine+ixabepilone which had enhanced efficacy over capecitabine+ixabepilone alone or with 13C4 (FIG. 3A). The combination of capecitabine and ixabepilone was more efficacious then capecitabine alone (FIG. 3B), however this combination was not more efficacious than ixabepilone therapy (FIG. 3C). Focusing on therapies involving 1D11, 1D11+capecitabine+ixabepilone was more efficacious than 1D11+ixabepilone, which was more efficacious than 1D11+capecitabine, which was more effective than 1D11 as a single agent (FIG. 4).

Figure 5:
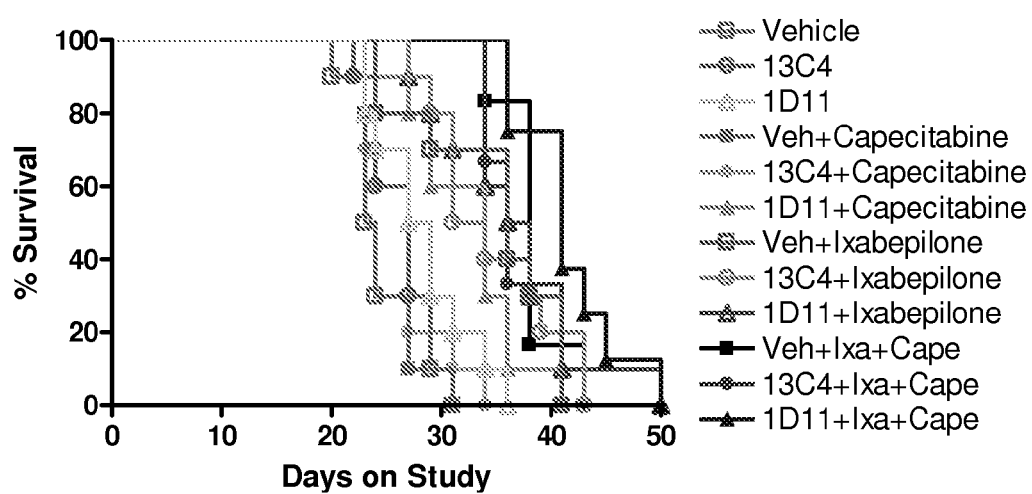
FIG. 5 shows the survival curve for animals. The longest median survival was observed in the animals treated with 1D11+capecitabine+ixabepilone.

Different treatment regimens had varying effects on survival. Mice treated with antibody therapies or capecitabine alone had similar survival curves (FIG. 5). Mice treated with ixabepilone alone or in combination with capecitabine had similar survival, which was greater than that of either the antibody or the capecitabine cohorts. 1D11 as a single agent did not enhance survival but 1D11+capecitabine had enhanced survival over capecitabine alone. 1D11 also did not enhance the survival benefit of ixabepilone alone, however the greatest median survival was observed in the 1D11+capecitabine+ixabepilone treatment group. Survival curves have also been affected by the toxicity due to chemotherapeutic regimens as described above.

Figure 6:
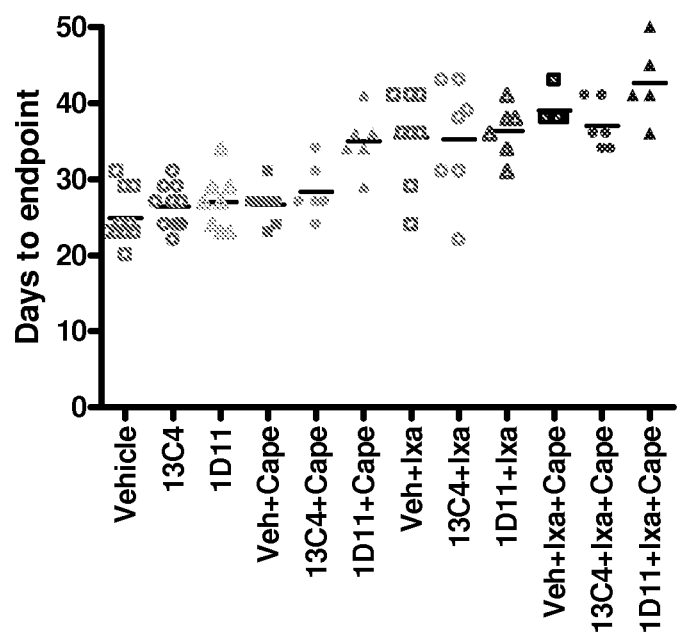
FIG. 6 shows the time taken to reach the endpoint of a primary tumor volume of ≥2000 mm$^3$ is significantly different ($p<0.0001$) between treatment groups. 1D11 increased the time to endpoint due to capecitabine therapy and the longest time to endpoint was achieved in the 1D11+capecitabine+ixabepilone group.

1D11 did not increase the time required to reach the size endpoint of 2000 mm$^3$ as a single agent and did not enhance the time to endpoint in ixabepilone-treated animals (FIG. 6). However, 1D11 enhanced the time to endpoint in the capecitabine cohort, and the longest time to endpoint in the study was observed in the 1D11+capecitabine+ixabepilone group.

Figure 7:
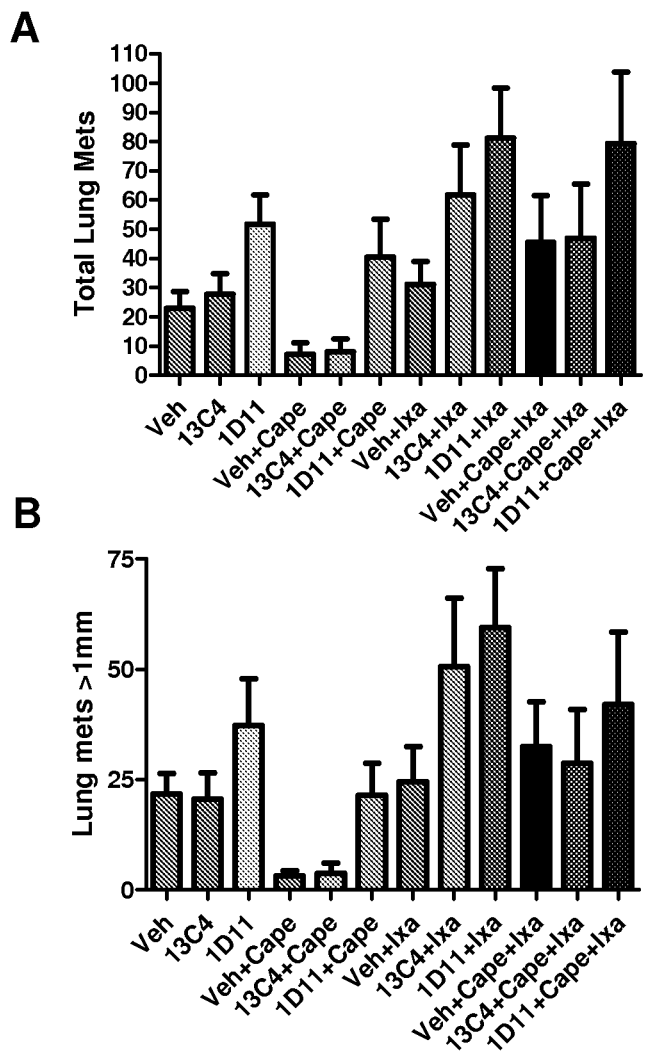
FIG. 7 shows the total number of lung metastases across all treatment groups (A) and the total number of lung metastases>1 mm in size across all treatment groups (B). The largest number of lung mets in each cohort was the treatment group with the longest time to endpoint; the 1D11 treatment group in each case.
Figure 8:
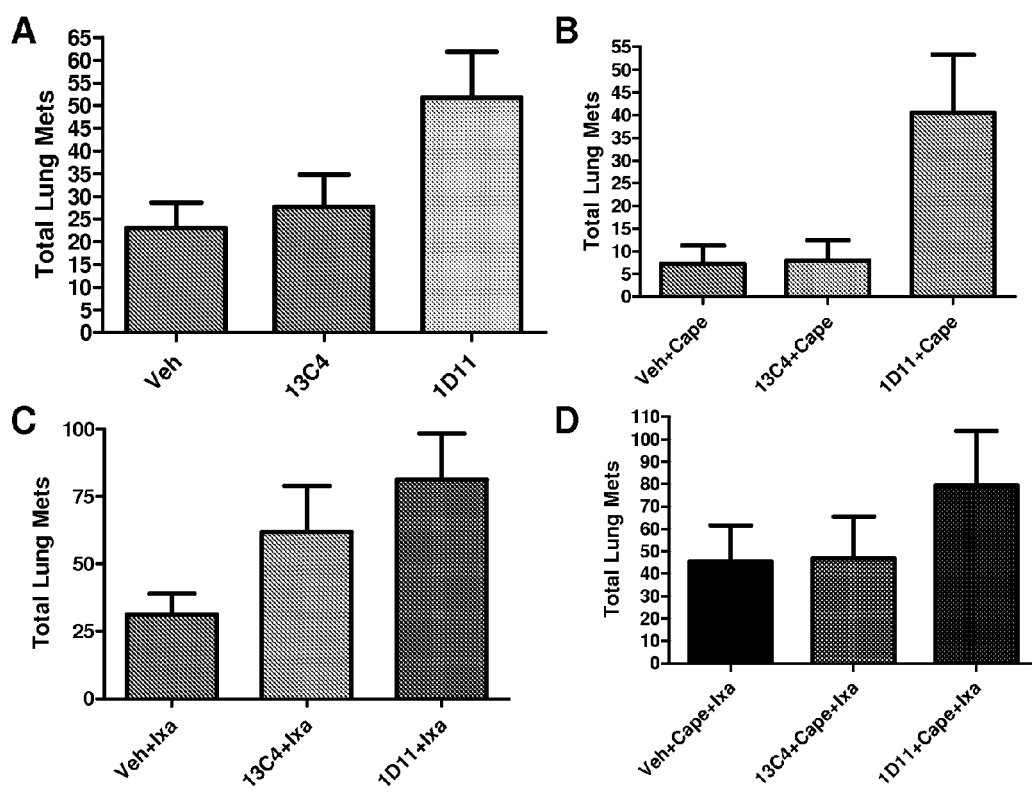
FIG. 8 shows the number of lung metastases in the single agent cohort (A), the capecitabine cohort (B), the ixabepilone cohort (C), and the capecitabine+ixabepilone cohort (D). In each cohort, the highest number of lung mets was observed in the 1D11 treatment group, likely because these treatment groups were on study longer than their respective controls within each cohort.
Figure 9:
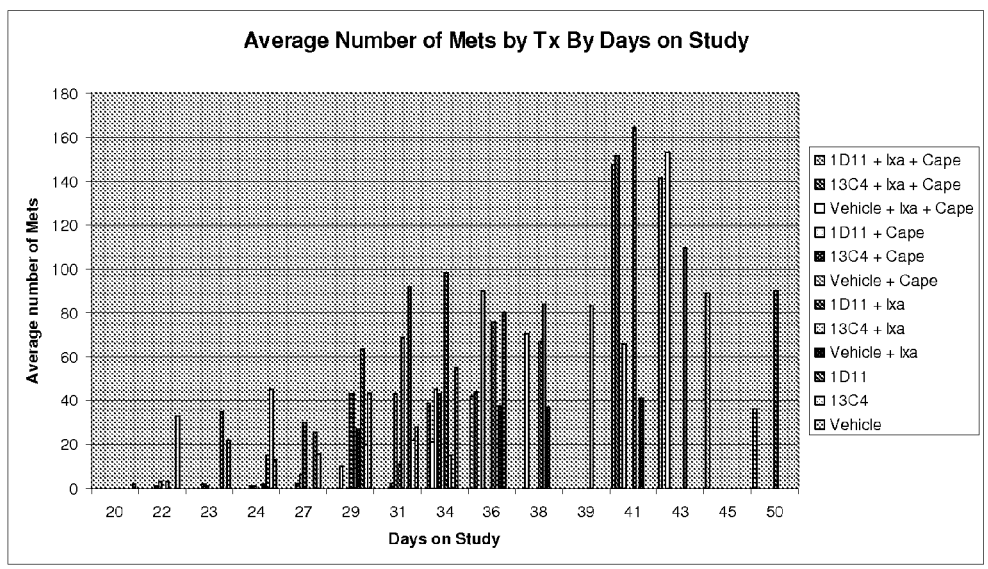
FIG. 9 shows that there was a correlation between the number of lung mets and the time on study, regardless of treatment.

Treatment with 1D11 led to an increase in metastasis to the lungs within each cohort (FIG. 7). The 1D11 single agent group had significant increases in number of lung metastases compared to the vehicle-treated group or the 13C4-treated group and similar increases due to 1D11 treatment were observed in the capecitabine, ixabepilone and capecitabine+ ixabepilone cohorts (FIG. 8). The number of lung mets increased as a function of the time that an animal was on study, and this effect was independent of the treatment group (FIG. 9).

In the clinic, the combinatorial therapy of ixabepilone and capecitabine has been reported to be more efficacious than capecitabine alone in taxane-resistant triple-negative breast cancer (TNBC). The 4T1 murine mammary carcinoma model is routinely uses as a good surrogate for human TNBC and for preclinical testing of therapeutics against TNBC. The purpose of Study was to determine whether 1D11 would enhance the efficacy of capecitabine, ixabepilone, or the combination of the two chemotherapeutics against primary tumor growth and/or subsequent metastasis in the syngeneic 4T1 model of TNBC.

As observed in previous studies with this model, 1D11 as a single agent did not significantly inhibit the growth of primary, SQ 4T1 tumors. However, 1D11 did enhance the efficacy of capecitabine and the combinatorial therapy of capecitabine+ixabepilone against primary tumors. In fact, the triple combination of 1D11+capecitabine+ixabepilone was most efficacious at inhibiting 4T1 primary tumor growth, and also provided the largest survival benefit and produced the longest time to endpoint. Taken together, this data suggests that combining a TGFβ neutralization strategy with capecitabine+ixabepilone therapy may provide a therapeutic benefit over treatment with capecitabine+ixabepilone alone.

This data represents the first enhancement of efficacy of a chemotherapeutic in the SQ 4T1 tumor model. Previously in this model, 1D11 has been combined with paclitaxel, cisplatin or carboplatin and in each of these studies, 1D11 did not improve the efficacy of the chemotherapeutic tested.

In this study, combining 1D11 with capecitabine enhanced the efficacy observed with capecitabine alone, suggesting that the enhanced efficacy in the 1D11+capecitabine+ixabepilone group over the capecitabine+ixabepilone group may be due to enhancement of capecitabine's effects on tumor growth. Capecitabine is an oral prodrug that is converted to 5-fluorouacil, which blocks DNA synthesis by acting as a pyrimidine mimic. The anti-tumor mechanism is similar to that of gemcitabine. Interestingly, 1D11 did not enhance the efficacy of gemcitabine in models of pancreatic cancer suggesting that the enhancement observed in this study is dependent on the specific drug, tumor model or both.

Surprisingly, treatment with 1D11 resulted in increased metastasis in each cohort rather than an enhancement of the effect of each chemotherapeutic.

In this study, treatment-related toxicities such as weight loss, a scruffy and hunched appearance and difficulty breathing were observed in mice receiving the chemo-combo therapies. Mice receiving ixabepilone displayed peripheral neuropathy in the form of hind limb immobility that was resolved once the treatment therapy was completed. 1D11 had no effect on the incidence or severity of these toxicities.

Example 2

Study 2: The Effects of 1D11, Ixabepilone, Capecitabine and Combinations of these Therapeutics on Primary Tumor Growth and Metastases in a Syngeneic Triple-Negative Breast Cancer Model (4T1)

Experimental Methods:

Treatment groups, time points, and tissues were similar to the study described above. On Day 0, 150 twelve week-old female Balb/c mice each received subcutaneous injections of 50,000 4T1 cells in Matrigel in the right flank. Tumor-bearing mice were routinely monitored and regular tumor measurements were conducted 2-3×/week beginning on Day 6. Tumor volume was determined using the following formula:

$$\text{Tumor Volume} = \text{Length} \times \text{Width}^2 \times 0.52$$

Figure 10:
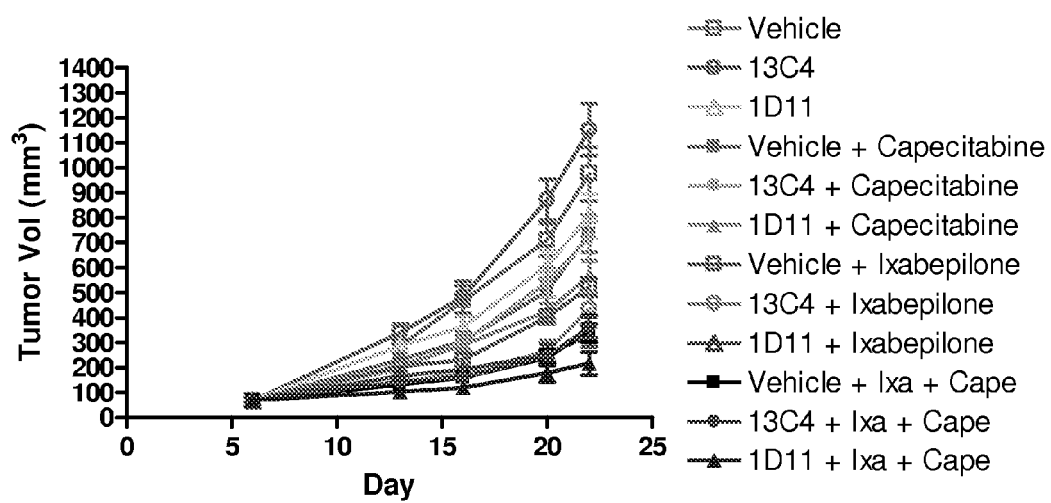
FIG. 10 shows mean primary tumor volumes. Inhibition of tumor growth was observed in the capecitabine, ixabepilone, and capecitabine+ixabepilone cohorts compared to the antibody only cohort.

Six days after tumor cell injection, when tumor volumes averaged ~70 mm³, the animals were size-matched and divided into twelve treatment groups of ten mice each. Thirty mice with primary tumors that were either significantly larger that the average or were non-palpable (0 mm³) were removed from the study. At this point investigators were blinded to treatment group designations and therapeutic administration was initiated. All mice received 10 mg/kg of either 1D11, 13C4 or antibody vehicle administered in 100 µl IP three times per week (FIG. 10). Specific cohorts of mice received additional treatments of ixabepilone (3 mg/kg in 200 µl Q4D×3), capecitabine (360 mg/kg in 100 µl by oral gavage QD×14) or both.

Mice were monitored for excessive ulceration or presentation of moribund conditions (lack of grooming, labored breathing, cachexia, anorexia or lethargy). For proper analysis of metastasis, all mice were sacrificed on study Day 23. Upon sacrifice, gross necropsies were performed and tumors, lungs and other tissues bearing metastases were harvested. The primary tumor was bisected, with one half frozen in OCT and the other half stored in RNA Later for qPCR analysis. The lungs were fixed in zinc-buffered formalin for enumeration of pulmonary mets and subsequent IHC analysis.

Results:

By Study Day 23, mice had received eight treatments of antibody vehicle, 13C4 or 1D11. There were no toxicity issues observed during the dosing of either the ixabepilone, capecitabine or antibody therapeutics in this study. All animals were taken down on Study Day 23 except for one mouse that was sacrificed prior to the takedown because the tumor became ulcerated.

Tumors in this study grew at a slightly slower rate than in previous studies, and consequently were comparatively small when the study was terminated at Study Day 23.

Figure 11:
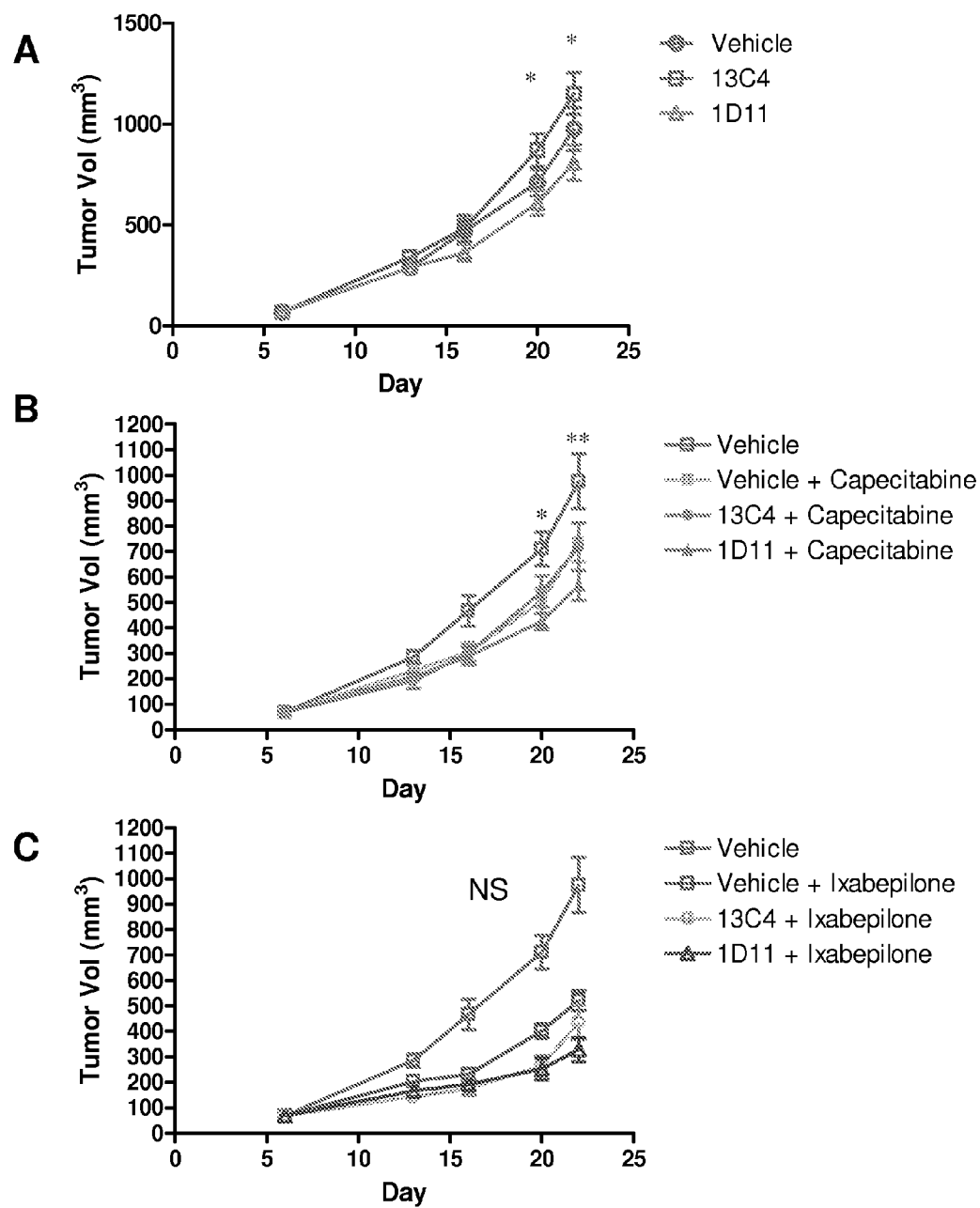
FIG. 11 shows that treatment with 1D11 had slight effects as a single agent or in combination with either capecitabine or ixabepilone. A. Single agent therapy with 1D11 resulted in a significant reduction in primary tumor size. B. 1D11, administered in combination with capecitabine, resulted in enhanced efficacy above that of capecitabine alone. C. 1D11 did not enhance the efficacy of ixabepilone in a statistically significant manner. (A: *=$p<0.05$, Tukey's Multiple Comparison Test) (B: *=$p<0.05$, **=$p<0.01$, T-Test).

Despite the reduced tumor size in this study, clear differences were observed between the mean tumor volumes among treatment groups (FIGS. 10&11). Notably, a significant reduction in tumor volume was present on Study Days 20 and 22 when comparing animals dosed with 1D11 as a single agent with those that received 13C4 alone though the 1D11 treatment resulted in a statistically insignificant trend of growth inhibition due to 1D11 compared to vehicle-treated animals (FIG. 11A). Treatment with capecitabine resulted in a trend towards inhibited growth of the primary tumors and a significant reduction in tumor volume was observed upon treatment with ixabepilone. The addition of 1D11 to capecitabine therapy resulted in a statistically insignificant trend towards enhanced efficacy over capecitabine alone (FIG. 11B). Combining 1D11 with ixabepilone resulted in enhanced efficacy compared to ixabepilone alone but when compared to 13C4+ixabepilone (FIG. 11C).

Figure 12:
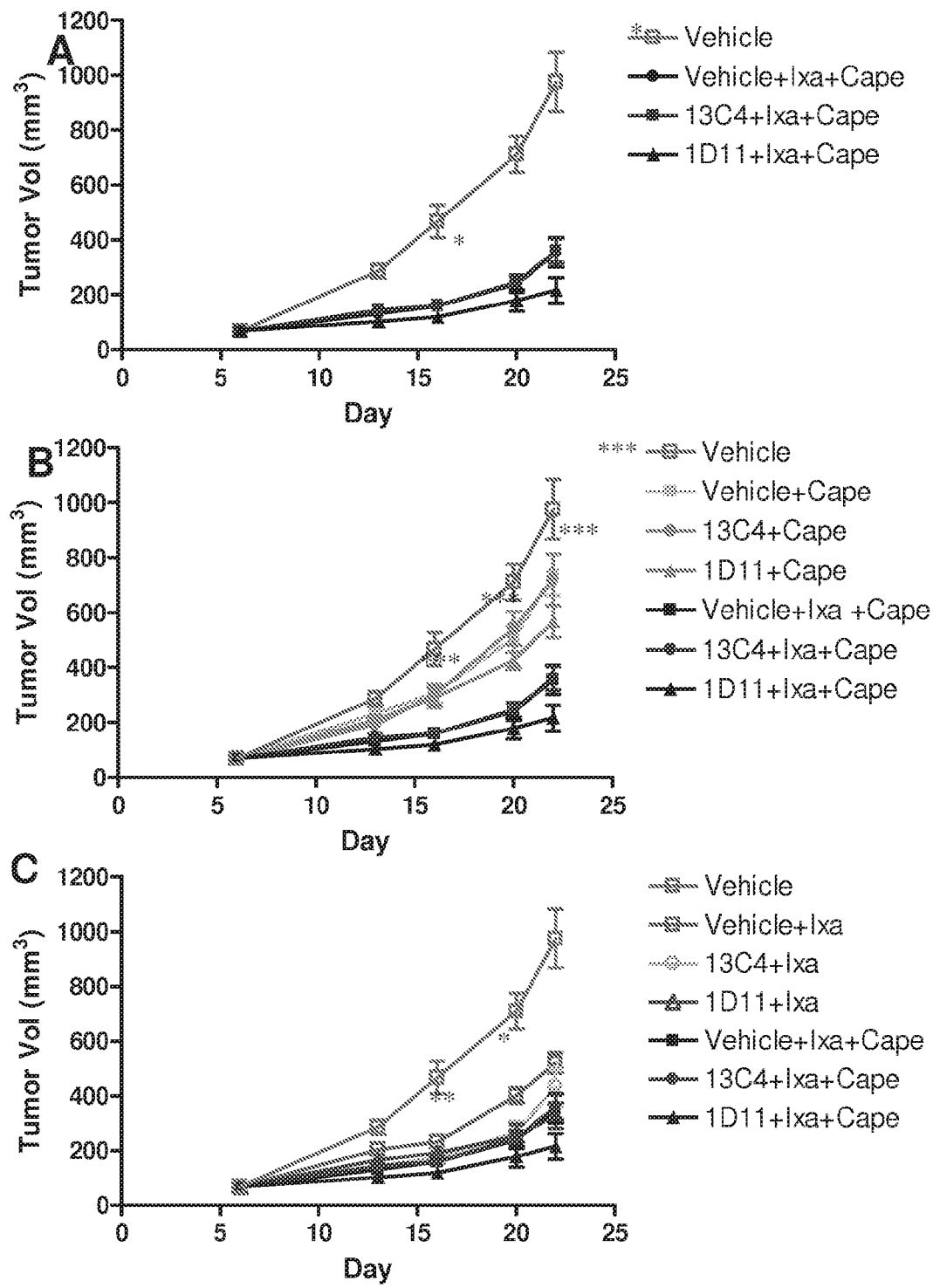
FIG. 12 shows that therapy with 1D11 significantly enhanced the efficacy of the ixabepilone/capecitabine combination against primary tumor volume. A. 1D11 enhanced the efficacy of ixabepilone and capecitabine when compared to 13C4 combined with ixabepilone and capecitabine. B. Ixabepilone significantly enhanced the efficacy of 1D11 and capecitabine when dosed together. C. The triple combination of 1D11, capecitabine and ixabepilone was more efficacious than 1D11+ixabepilone. (A: *=$p<0.05$, T-Test) (B: ***=$p<0.001$, One-Way Anova) (C: *=$p<0.05$, T-Test)
Figure 13:
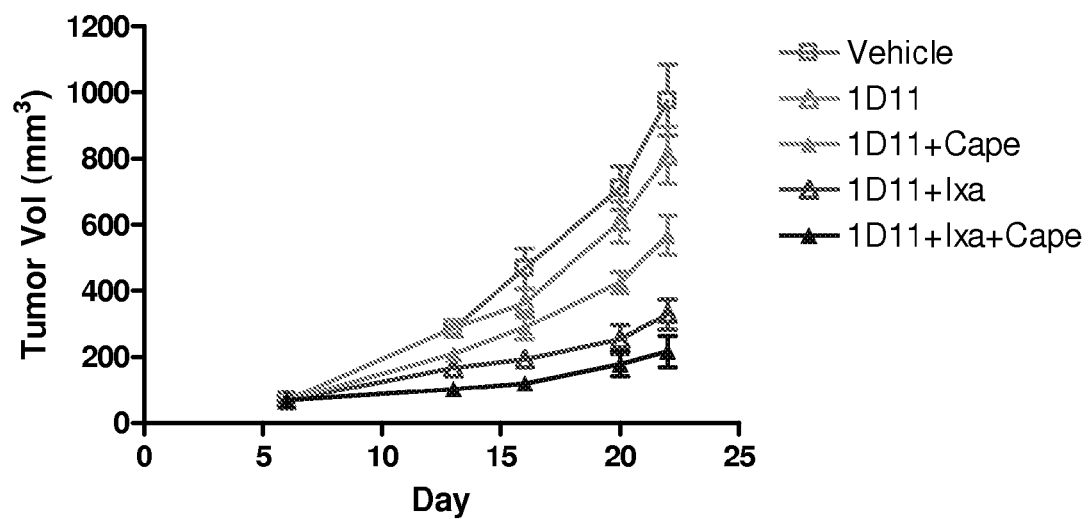
FIG. 13 shows an overview of the effects of 1D11 as a single agent or in combination with capecitabine and/or ixabepilone on 4T1 tumor growth. The most effective therapy is the triple combination of 1D11+capecitabine+ixabepilone.

The added benefit of combining ixabepilone and capecitabine over either chemotherapeutic alone observed in Study 09-3493 was confirmed in this study (FIG. 12A). The combinatorial therapy of capecitabine and ixabepilone was significantly more efficacious at inhibiting SQ 4T1 tumor growth than capecitabine (FIG. 12B), and there was a slight benefit over ixabepilone alone (FIG. 12C). The strongest inhibition of tumor growth was observed in mice receiving the combinatorial therapy of 1D11+capecitabine+ixabepilone which had enhanced efficacy over capecitabine+ixabepilone alone or with 13C4 (FIG. 12A), confirming the data from Study 09-3493. Focusing on therapies involving 1D11, 1D11+capecitabine+ixabepilone was more efficacious than 1D11+ixabepilone, which was more efficacious than 1D11+capecitabine which was more effective than 1D11 as a single agent (FIG. 13).

Figure 14:
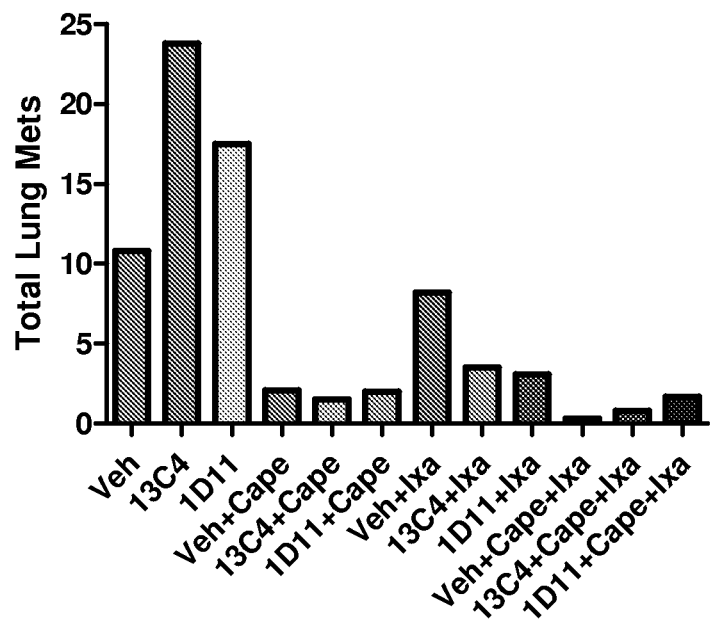
FIG. 14 shows total lung metastases. 1D11 did not inhibit the number of metastases to the lung nor enhance the efficacy of chemotherapeutics.

Treatment with 1D11 did not inhibit the number of pulmonary metastases as a single agent (FIG. 14). Metastasis was significantly decreased in cohorts receiving combinatorial therapies and the average number of mets in each of these cohorts was less than 10. Both 1D11+ixabepilone and 13C4+ixabepilone reduced the number of mets compared to capecitabine, but there were no differences among treatment groups in the capecitabine or the capecitabine+ixabepilone cohorts.

This study is the second study to determine the effect of adding 1D11 to the combination of the chemotherapeutics ixabepilone and capecitabine on inhibiting primary tumor growth and preventing lung metastasis. Similar to the first study, 09-3493, 1D11 did not have much of an effect on primary tumor growth as a single agent. There was a trend towards inhibition in the 1D11 group when compared to the 13C4-treated group, but this significance was lost when compared to the vehicle-treated group. There were also trends showing that 1D11 enhanced the efficacy of capecitabine and ixabepilone, although in the latter case, the enhancement of ixabepilone's efficacy was similar to that by 13C4. However, in this study, as in 09-3493, the most significant inhibition of 4T1 tumor growth was observed in the mice treated with 1D11+capecitabine+ixabepilone. The enhancement of efficacy was evident even though the animals were taken down at a time point where the separation among treatment groups was just beginning to occur. Taken together, the data from these two studies clearly demonstrate that combining a TGFβ neutralization strategy with capecitabine+ixabepilone therapy may provide a therapeutic benefit over treatment with capecitabine+ixabepilone alone.

Taken together, the data from these two studies represents the first enhancement of efficacy of a chemotherapeutic in the SQ 4T1 tumor model. Previously in this model, 1D11 has been combined with paclitaxel, cisplatin or carboplatin and in each of these studies, 1D11 did not improve the efficacy of the chemotherapeutic tested.

In Study 09-3493, the enhancement of the efficacy of capecitabine+ixabepilone could possibly be attributed to enhancement of capecitabine's efficacy since 1D11 enhanced the efficacy of capecitabine alone but not that of ixabepilone. In this study there was a trend towards enhancement of efficacy by 1D11 in the capecitabine cohort but it was not statistically significant. 1D11 appeared to enhance the efficacy of ixabepilone but a similar result was observed when ixabepilone was combined with 13C4. It is likely that there would have been better separation of the treatment groups in each cohort had the study been carried out longer. This will have to be addressed in upcoming studies in order to determine if the enhancement of the efficacy of capecitabine+ixabepilone by 1D11 was due to the enhancement of the activity of capecitabine, ixabepilone or is merely a function of when 1D11 is combined with both therapeutics.

In Study 09-3493, animals receiving 6 mg/kg ixabepilone typically displayed peripheral neuropathy, and many in the ixabepilone+capecitabine cohort became moribund due to the therapy and had to be sacrificed. In this study, the dose of ixabepilone was lowered from 6 mg/kg to 3 mg/kg; a dose which showed efficacy against 4T1 tumor growth in the MTD study run through Pharm/Tox. With this reduced dose of ixabepilone, no animals in the study displayed signs of toxicity at any point during the study. Additionally, the 3 mg/kg dose proved to be efficacious against primary tumor growth and/or metastatic incidence in this study. As such, utilizing this lower dose would likely be advantageous in future studies due to the reduced toxicity.

In addition to being able to observe effects on primary tumor growth, this study was designed in such a manner that the effects of 1D11 as a single agent or in combination with chemotherapeutics on metastasis from the SQ 4T1 primary tumor to the lungs would also be discernible. Animals were all taken down at Day 23 rather than when each individual tumor reached 2000 mm$^3$ (as in Study 09-3493) in order to eliminate the possibility of a longer duration of tumor growth leading to more metastases. Surprisingly, 1D11 did not inhibit metastasis in this study as had been observed in other tumor models including the 4T1 intracardiac model of experimental metastasis. It should be noted however, that the number of lung mets in the single agent antibody cohort was low in each treatment group and especially low in the chemo-combo cohorts, indicating that perhaps these animals were taken down earlier than they should have been. The average size of the tumors at the time of study take down was ~1000 mm$^3$ in the antibody cohort, ~700 mm$^3$ in the capecitabine cohort and at or below 500 mm$^3$ in the ixabepilone and ixabepilone+capecitabine cohorts. The vast majority of the metastases present were less than 1 mm in size among all cohorts. In previous studies, reliable numbers of metastases (50-100 per set of lungs) were not present until the primary tumors reached ~1500 mm$^3$.

Example 3

Study 3: The Effects of 1D11, Ixabepilone, Capecitabine and Combinations of these Therapeutics on Primary Tumor Growth and Metastases in a Syngeneic Triple-Negative Breast Cancer Model (4T1)

Experimental Methods:

On Day 0, 150 twelve week-old female BALB/c mice each received subcutaneous injections of 50,000 4T1 cells in Matrigel in the right flank. Tumor-bearing mice were routinely monitored and regular tumor measurements 2-3×/week began on Day 6. Tumor volume was determined using the following formula:

Tumor Volume=Length×Width$^2$×0.52

Six days after tumor cell injection, the animals were size-matched and divided into twelve treatment groups of ten mice each. The remaining 30 animals were included into a companion experiment to this study, looking for the effects of 1D11 on macrophage recruitment and activity (see below). At this point investigators were blinded to treatment group designations and therapeutic administration was initiated. All groups of mice received treatments of either antibody vehicle, 1D11 or 13C4 administered in 100 μl IP three times per week. Specific cohorts of mice received additional treatments of capecitabine (360 mg/kg in 100 μl by oral gavage for 14 consecutive days), ixabepilone (3 mg/kg in 200 μl IV every four days for three treatments) or both.

An entire cohort of mice was sacrificed when the average tumor volume for a single group within that cohort reached 1500 m$^3$ or greater. Individual mice were sacrificed before that size endpoint if the tumors became ulcerated or if the animals presented with moribund conditions (lack of grooming, labored breathing, cachexia, anorexia or lethargy). Upon sacrifice, gross necropsies were performed and tumors, lungs and other tissues bearing metastases were harvested. A portion of the primary tumor was frozen in OCT for IHC of immunomarkers, and the remaining tumor and other tissues bearing metastases were fixed in zinc-formalin for paraffin embedding.

TABLE 3

Study outline for arginase experiments

| Group # | Treatment Groups | Animals per group |
|---|---|---|
| 13 | Antibody Vehicle | 10 |
| 14 | 13C4 10 mg/kg | 10 |
| 15 | 1D11 10 mg/kg | 10 |

Time points: Day 0: Investigators to inject 50,000 4T1 cells + matrigel subcutaneously in the right flank Day 3: Investigators to begin 2-3X/week tumor measurements Day 6: DCM Staff to begin antibody dosing IP 3X/week; seven total treatments Day 21: Group 13-15 mice sacrificed and primary tumors harvested
Tissues: Primary tumors in RPMI 1640 + 10% FBS maintained on wet ice.

The thirty mice that were not placed on the chemo-combo portion of this study, were size-matched and divided into three additional groups treated with antibody vehicle, 13C4 or 1D11 to evaluate the presence of M2 macrophages at the site of the primary tumor (Table 3). Primary tumors were collected from these mice on study day 21. Tumors were enzymatically digested in 5 ml Hank's Balanced Salt Solution (HBSS) containing 50 μg/ml collagenase I, 50 μg/ml collagenase IV, 25 μg/ml hyaluronidase, 10 μg/ml DNase 1 and 0.2 U/ml trypsin inhibitor. Tissues were incubated twice in the enzyme solution for 20 minutes at 37° C. with constant rocking and a cell suspension was created using the gentleMACS tissue dissociator. The disassociated cells and remaining tissue was passed through a 100 μm strainer then a 40 μm strainer into 50 ml centrifuge tubes. The cells were washed twice with HBSS and viable cells were counted. To enrich for CD11b$^+$ cells, viable cells were adjusted to 1.0×10$^7$ cells per 90 μl of degassed PBS containing 0.5% endotoxin-free BSA and 2 mM EDTA and incubated with anti-CD11b magnetic microspheres. CD11b$^+$ cells were positively selected using the AutoMacs Pro Separator. Portions of single CD11b+ cell suspensions were stained for CD11b, F4/80, CD206 and Gr-1. The remaining CD11b$^+$ cells were lysed to extract arginase.

For the cellular arginase assay, enriched cells were washed with PBS and 1.0×10$^6$ cells from each tissue were added to separate 0.5 ml microcentrifuge tubes. The cells were washed with PBS at 1000 g at 4° C. and the pelleted cells were lysed for 10 minutes in 10 mM Tris-HCl (pH 7.4) containing 0.4% Triton X-100 and protease inhibitor. Lysates were centrifuged at 14,000 g and supernatants were stored at −80° C. until date of assay. Arginase levels, as determined by measuring the conversion of arginine to ornithine and urea against a urea standard curve, were quantified using the Quantichrome Arginase Kit (BioAssay System).

Figure 15:
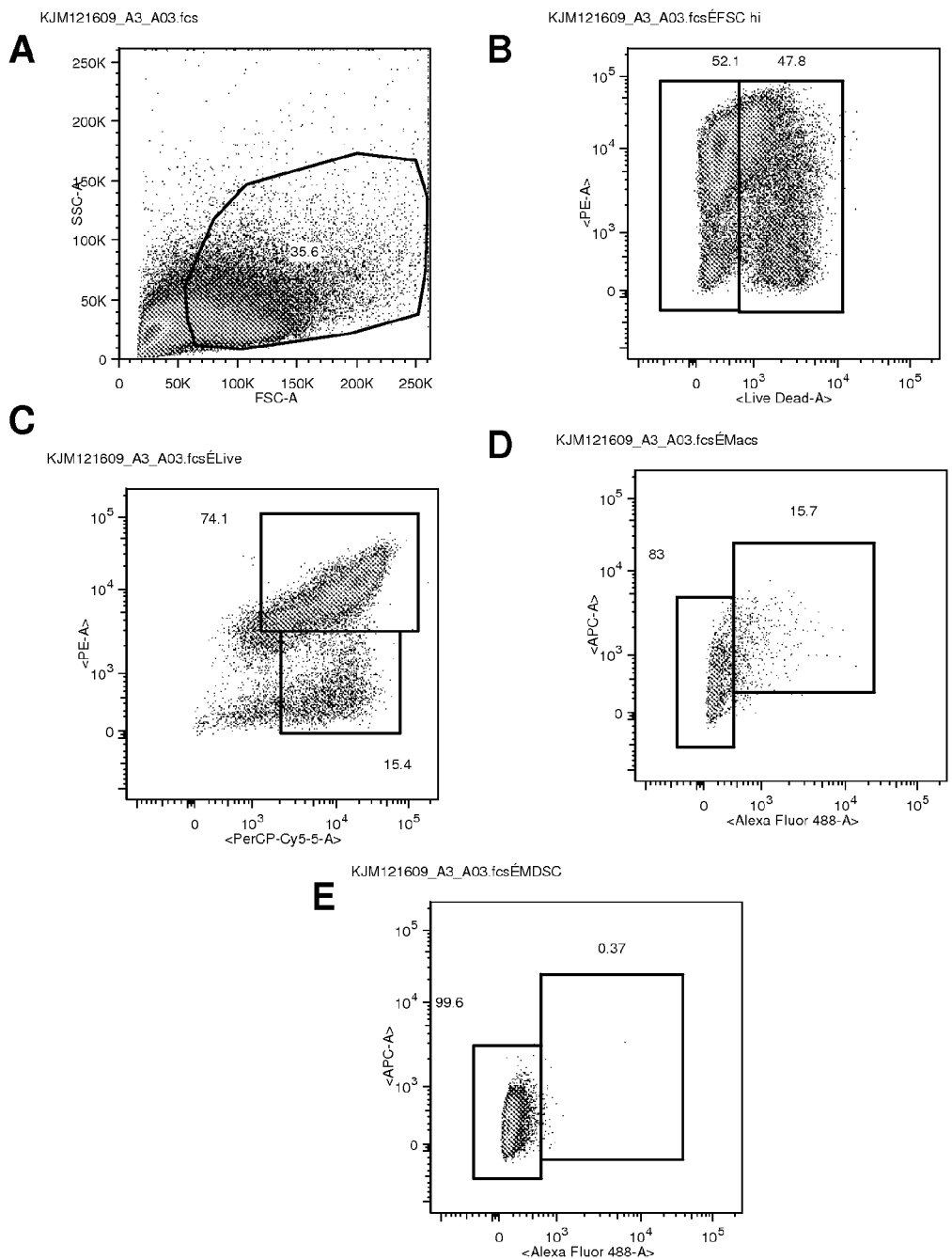
FIG. 15 shows gating scheme of CD11b$^+$ cells isolated from 4T1 primary tumors. (A) FSC hi gating of cells based on size and scatter. (B) Live gate (dim, 52%) of viable cells through the FSC hi gate. (C) Gating of MDSCs (Gr-1 PE bright CD11b PerCP Cy5.5 bright, 74.1%) and macrophages (Gr-1 PE dim and CD11b PerCP Cy5.5 bright, 15.4%) through the live gate (D) Gating of M1 macrophages (F4/80 bright and CD206 Alexa 488 dim, 83%) and M2 macrophages (F4/80 bright and CD206 Alexa 488 bright, 15.7%) gated through macrophages (E) Confirmation of CD206 negative/low status of MDC gated through Gr-1$^+$CD11b$^+$.

For cell immunophenotyping, 1.0×10$^6$ cells from each tissue were blocked with 10 μg/ml Fc Block (anti-CD16/32) for 30 minutes prior to staining with antibodies for myeloid derived cells (CD11b), macrophages (F4/80), M2 macrophages (CD206) and MDSCs (Gr-1). Cell viability was determined using Live/Dead Fixable Dead Cell Stain (Invitrogen). The cells were fixed for 15 minutes in 1% paraformaldehyde and events were acquired on a BD LSR II flow cytometer. Data analysis was performed using Flow Jo software (FIG. 15).

Figure 16:
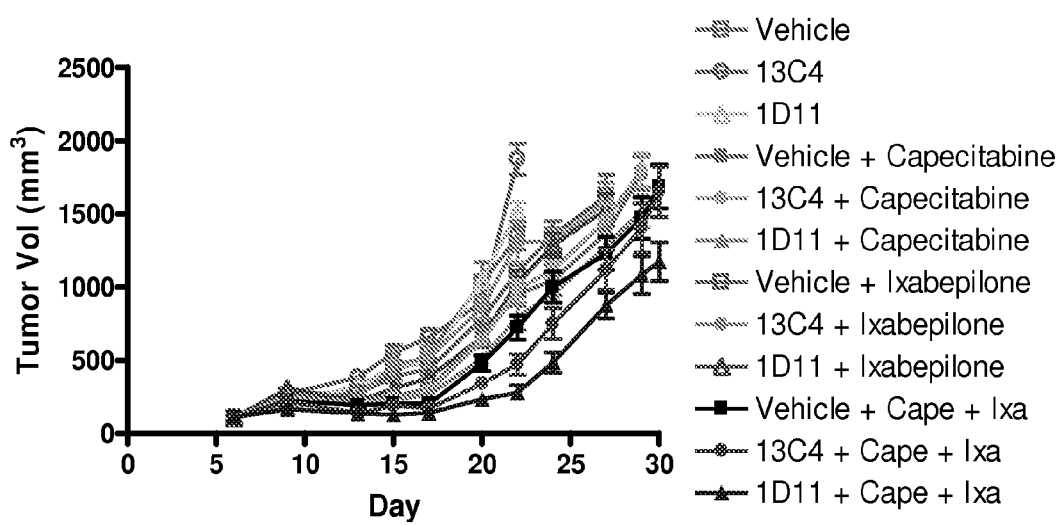
FIG. 16 shows mean primary tumor volumes. Inhibition of tumor growth was observed in the capecitabine, ixabepilone and capecitabine+ixabepilone cohorts compared to the antibody only cohort.

Results:

There were differential effects on tumor growth depending on the treatment provided with the fastest tumor growth observed in mice treated with antibody therapy alone, and the slowest growth in mice treated with antibody+capecitabine+ixabepilone (FIG. 16). In this study, an entire cohort of animals was sacrificed on the day that the average tumor volume in that cohort reached a size endpoint of 1500 mm$^3$. Mice in the antibody therapy alone cohort reached a mean tumor volume of ~1500 mm$^3$ by study day 23. The capecitabine and ixabepilone cohorts demonstrated delayed tumor growth reaching endpoint on study day 27 and 29 respectively, while the combination of capecitabine and ixabepilone had the longest delay as this cohort reached endpoint at 30 days.

Figure 17:
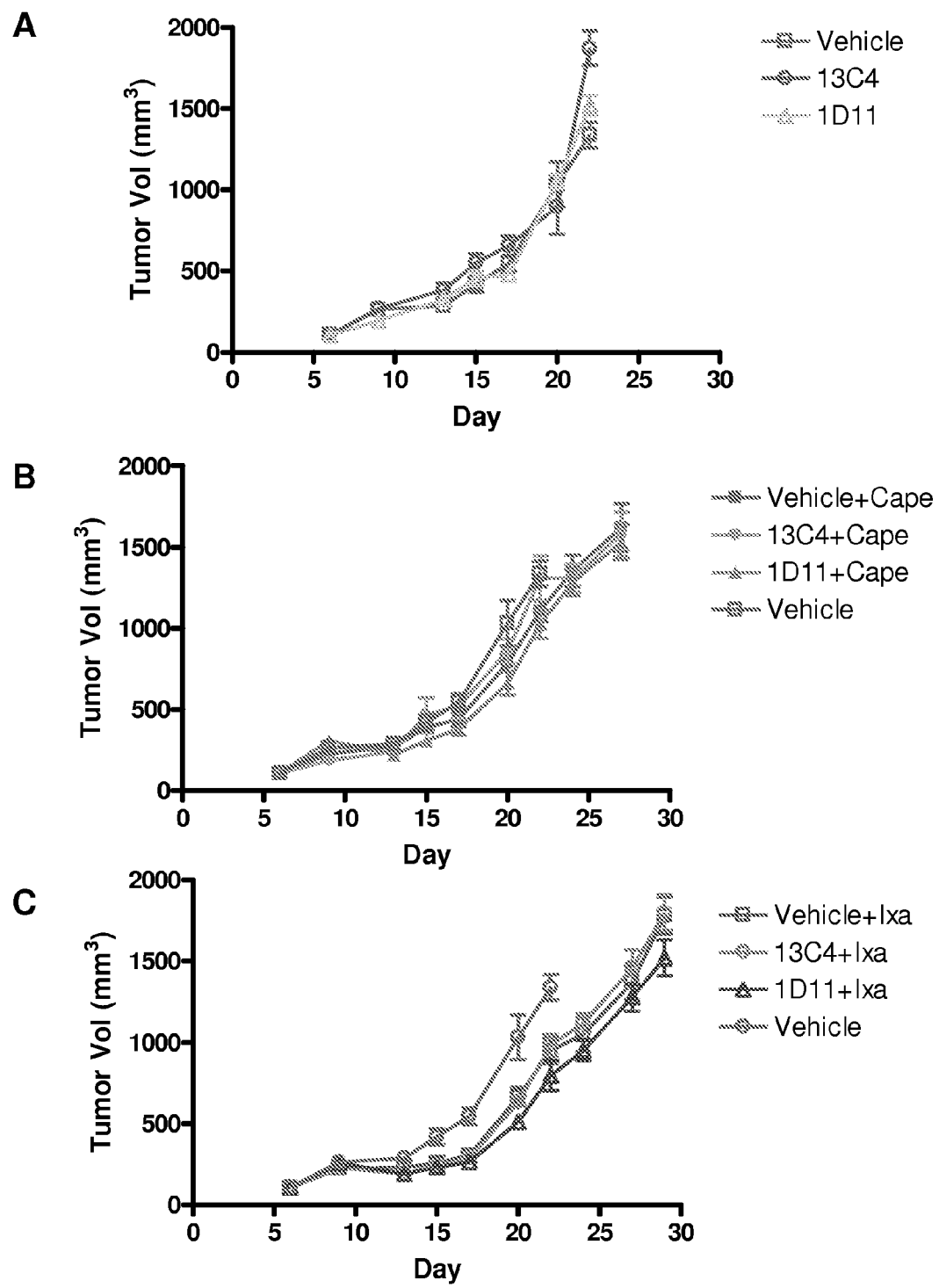
FIG. 17 shows that 1D11 as a single agent had no effect on 4T1 tumor growth (A). 1D11 also did not significantly enhance the efficacy of capecitabine (B) or ixabepilone (C).

As a single agent, 1D11 had no significant effect on the growth of SQ 4T1 tumors (FIG. 17A). Treatment with capecitabine resulted in very modest tumor growth inhibition, and ixabepilone was most efficacious at inhibiting 4T1 tumor growth as a monotherapy. The addition of 1D11 did not enhance the efficacy of either capecitabine (FIG. 17B) or ixabepilone (FIG. 17C).

Figure 18:
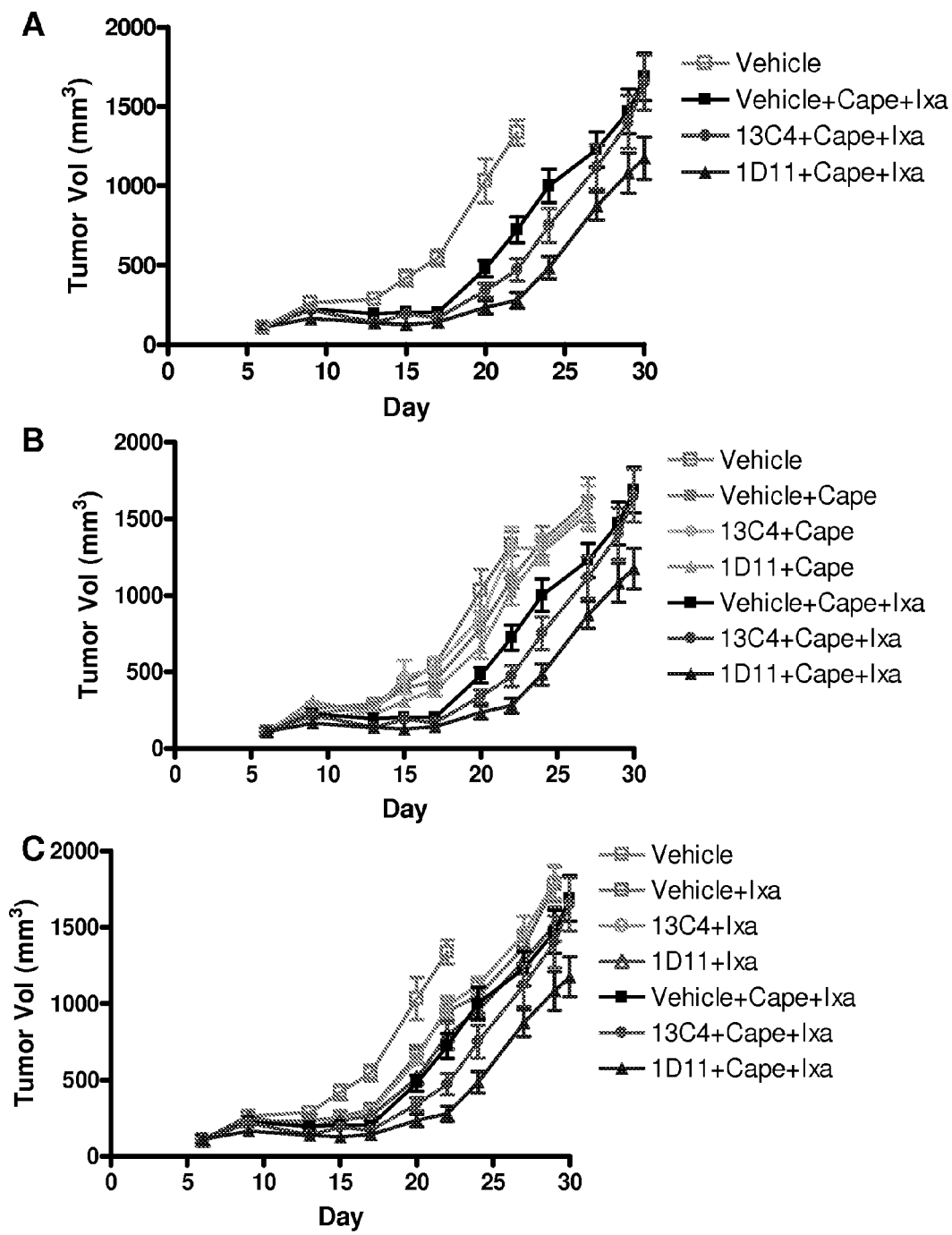
FIG. 18 shows that 1D11 enhanced the efficacy of the combinatorial therapy of capecitabine+ixabepilone in inhibiting 4T1 tumor growth (A). Capecitabine inhibited 4T1 tumor growth slightly but was more efficacious when combined with ixabepilone (B). Tumor growth inhibition between ixabepilone and the capecitabine+ixabepilone combination therapy was similar unless 1D11 was also included in the combinatorial therapy (C).
Figure 19:
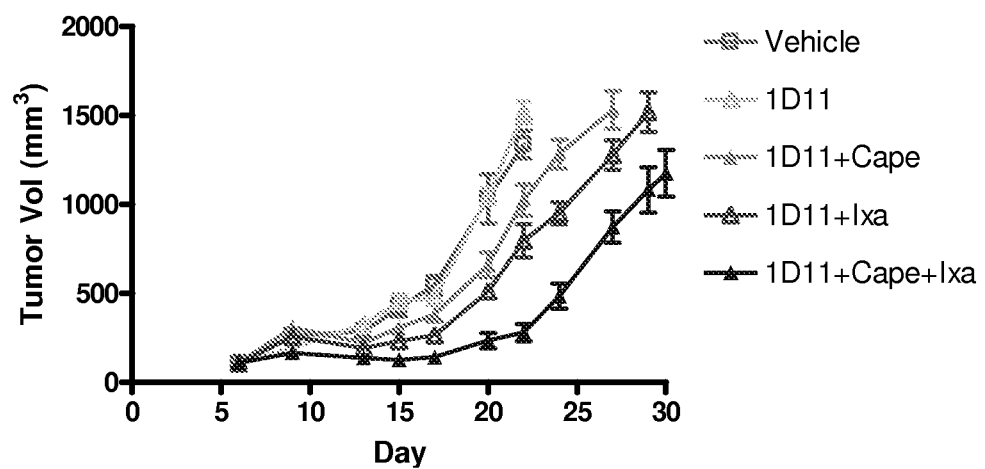
FIG. 19 shows an overview of the effects of 1D11 as a single agent or in combination with capecitabine and/or ixabepilone on 4T1 tumor growth. The most effective therapy is the triple combination of 1D11+capecitabine+ixabepilone.

The strongest inhibition of tumor growth was observed in mice receiving the combinatorial therapy of 1D11+capecitabine+ixabepilone which had enhanced efficacy over capecitabine+ixabepilone alone or with 13C4 (FIG. 18A). Very striking is that the combination of 1D11, capecitabine and ixabepilone resulted in the smallest mean tumor volume, 1174.50 mm$^3$, at time of sacrifice compared to the vehicle (1689.06 mm$^3$) and 13C4 (1651.24 mm$^3$) combo treatment groups in this cohort. The combination of capecitabine and ixabepilone was more efficacious then capecitabine alone (FIG. 18B), however this combination was only slightly more efficacious than ixabepilone therapy (FIG. 18C). Focusing on therapies involving 1D11, 1D11+capecitabine+ixabepilone was more efficacious than 1D11+ixabepilone, which was more efficacious than 1D11+capecitabine, which was more effective than 1D11 as a single agent (FIG. 19).

Figure 20:
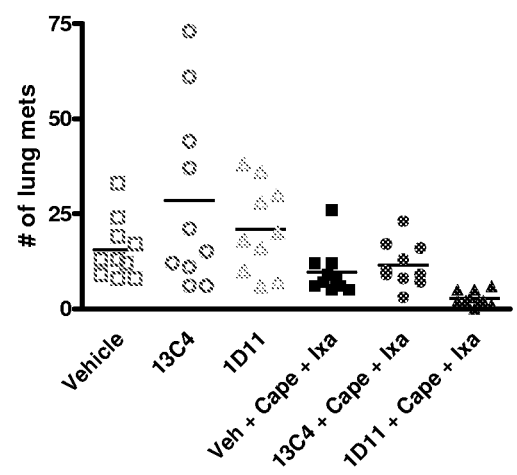
FIG. 20 shows that pulmonary metastases of mice bearing SQ 4T1 tumors were decreased by the combinatorial therapy of capecitabine+ixabepilone and the efficacy of this treatment was significantly enhanced by the addition of 1D11.

1D11 had no effect on the number of metastases that developed in the lungs of mice bearing SQ primary 4T1 tumors. Treatment with capecitabine+ixabepilone inhibited metastasis and the efficacy of this combinatorial therapy was significantly enhanced by 1D11 (FIG. 20).

TABLE 4

Percentage of total MDSC and macrophages from CD11b$^+$ cells isolated from 4T1 primary tumors

| | Antibody vehicle | 10 mg/kg 13C4 | 10 mg/kg 1D11 |
|---|---|---|---|
| 4T1 primary tumors (total macrophages) | 22% | 23% | 26% |
| 4T1 primary tumors (MDSC) | 72% | 71% | 64% |
| Total % of CD11b$^+$ cells | 94% | 94% | 90% |

Figure 21:
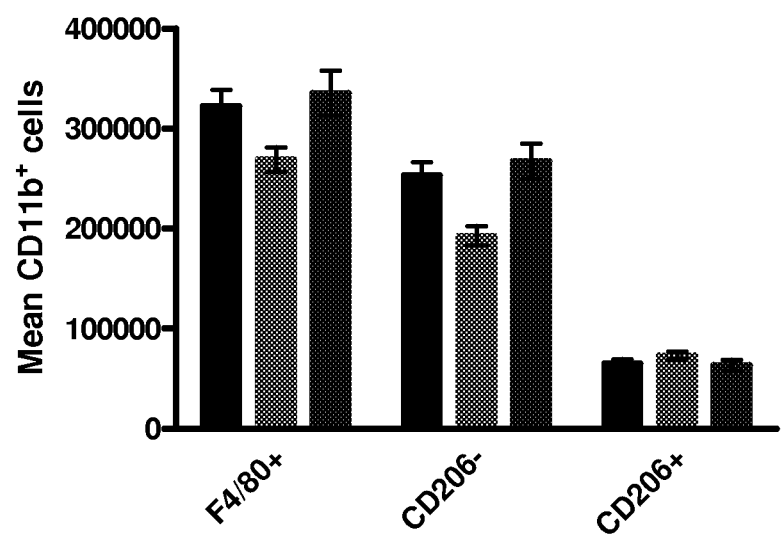
FIG. 21 shows that based on immunophenotyping of total macrophages (F4/80$^+$), M1 macrophages (F480$^+$CD206$^-$) and M2 macrophages (F4/80$^+$CD206$^+$) isolated from 4T1 primary tumors in Study 09-4255, 1D11 had little effect on the number of macrophages in primary tumors. Bar in black represents vehicle; bar in red represents 13C4 (control); and bar in blue represents 1D11.

Immunophenotyping of total macrophages (CD11b$^+$, F4/80$^+$) M1 macrophages (CD11b$^+$, F4/80$^+$, CD206$^-$), M2 macrophages (CD11b$^+$, F4/80$^+$CD206$^+$) and MDSC (CD11b$^+$, Gr-1$^+$) revealed that the majority of CD11b$^+$ isolated from primary 4T1 tumors are MDSC (Table 1). There appears to be a slight increase in TAMs and a decrease in the number of MDSCs in primary tumors treated with 1D11 compared to controls. Quantitative measurement of total macrophages, M1 macrophages and M2 macrophages was done by back calculating to the total number of cells isolated from primary tumors collected from each individual mouse (FIG. 21). By this analysis, there was no significant difference on the number of macrophages between treatment groups. However, there is a trend of increased CD206$^-$ M1 macrophages from primary tumors (FIG. 21) of 1D11 treated mice.

Figure 22:
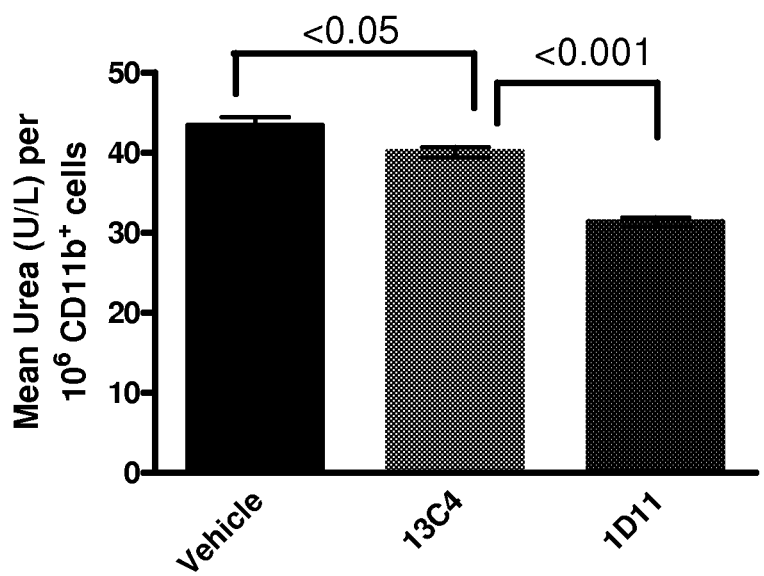
FIG. 22 shows that arginase from CD11b$^+$ cells isolated from 4T1 primary tumors from 1D11 treated mice is significantly decreased compared to control mice.

Although treatment with 1D11 did not decrease the number of M2 macrophages associated with the tumors, 1D11 appears to have an inhibitory effect on arginase production by TAMs. Arginase levels were significantly decreased from CD11b$^+$ cell lysates from 1D11 treated mice compared to controls (FIG. 22, p<0.001 by one-way ANOVA analysis, Tukey multiple comparison test).

In the clinic, the combinatorial therapy of ixabepilone and capecitabine has been reported to be more efficacious than capecitabine alone in taxane-resistant triple-negative breast cancer (TNBC). The 4T1 murine mammary carcinoma model is routinely uses as a good surrogate for human TNBC and for preclinical testing of therapeutics against TNBC. The purpose of earlier study was to determine whether 1D11 would enhance the efficacy of capecitabine, ixabepilone, or the combination of the two chemotherapeutics against primary tumor growth and/or subsequent metastasis in the syngeneic 4T1 model of TNBC.

This study was designed to determine if 1D11 could enhance the effect of the chemotherapeutics capecitabine and ixabepilone on inhibiting 4T1 primary tumor growth and metastasis from the primary tumor to the lungs. The strongest tumor growth inhibition was observed in the 1D11 plus capecitabine and ixabepilone treatment group. The combination of capecitabine and ixabepilone also inhibited metastasis to the lungs and this effect was further enhanced when 1D11 was added to the combinatorial therapy. As observed in previous studies with this model, 1D11 as a single agent had no effect on primary tumor growth, did not inhibit metastasis, and did not significantly enhance the efficacy of either capecitabine or ixabepilone when these were administered as monotherapies.

The results from Study 09-4255 confirm results from two previous studies, 09-3493 and 09-3494, that 1D11 can significantly enhance the efficacy of the combinatorial therapy of capecitabine and ixabepilone against 4T1 primary tumor growth and this study was the first to demonstrate that 1D11 could also enhance the inhibition of metastasis by capecitabine+ixabepilone. This data represents the first enhancement of efficacy of a chemotherapeutic in the SQ 4T1 tumor model. Previously in this model, 1D11 has been combined with paclitaxel, cisplatin or carboplatin, and in each of these studies, 1D11 did not improve the efficacy of the chemotherapeutic tested.

Since 1D11 as a single agent had no effect on either primary tumor growth or metastasis, the addition of 1D11 to capecitabine+ixabepilone results in a synergistic effect. The reason for this synergy is not yet known. 1D11 only enhances the efficacy of the combination of capecitabine and ixabepilone and 1D11 did not consistently enhance the efficacy of either capecitabine or ixabepilone when these chemotherapeutics were administered individually. The antitumor activity of capecitabine, a prodrug which is converted to 5-fluorouracil, is due to its ability to function as a pyrimidine antagonist and ixabepilone is a microtubule stabilizer. In the clinic, the combination of capecitabine and ixabepilone was more efficacious than either agent alone against triple-negative breast cancer. In the 4T1 tumor model, the efficacy of the combination therapy was stronger than capecitabine alone and was only marginally better than that observed with ixabepilone alone. Targeting TGFβ with 1D11 is hypothesized to enhance antitumor immunity by neutralizing the immunosuppressive effects of tumor and stroma-derived TGFβ. It is possible that these potentially subtle effects in such an aggressive tumor model can only enhance chemotherapeutic efficacy when the tumors are attacked by multiple therapeutics targeting multiple pathways.

In study 09-3493, significant toxicity was observed in tumor-bearing animals treated with the combination of capecitabine and ixabepilone. The doses of each therapeutic were 360 mg/kg and 6 mg/kg, respectively. The dose of ixabepilone, which can lead to neuropathy, was reduced to 3 mg/kg in the second study in this series, 09-3494. This resulted in a significant reduction in toxicity and neuropathy, and therefore this dose was used in the present study. Even though weight loss was observed in mice receiving antibody/chemotherapeutic treatment, there was a significant reduction of severe adverse events such as hind limb paralysis and death that was observed in Study 09-3493. Weight loss was the most common side effect of the combinatorial therapy, however the addition of 1D11 did not increase or decrease the incidence of this toxicity.

Taken together, this data shows that combining a TGFβ neutralization strategy with capecitabine+ixabepilone therapy will provide a therapeutic benefit over treatment with capecitabine+ixabepilone alone in the clinic.

Given the efficacy we see with 1D11 against metastasis in other tumor models and the enhancement of capecitabine+ixabepilone in this series of studies, several studies have been conducted investigating the mechanism of action of 1D11. It was found that cytotoxic T lymphocytes (CTLs) are critical for the ability of 1D11 to inhibit metastasis in the B16-F10 footpad tumor model of spontaneous metastasis. In Study 09-4255, a companion experiment to the main efficacy study was conducted to determine if neutralization of TGFβ by 1D11 is affecting the recruitment, phenotype, and/or activity of TAMs.

Classically activated TAMs also know as M1 macrophages, are tumoricidal in part through inducible NO synthase (iNOS). Conversely, alternatively activated TAMs, or M2 macrophages, have been associated with tumor progression by promoting tumor invasion, metastasis and angiogenesis. It has been reported in the literature that M2 macrophages secrete arginase and are capable of promoting tumor cell proliferation through the arginase pathway. Another cell type, MDSCs, is recruited to the site of primary tumors where they play an immunosuppressive role. MDSCs and macrophages are also large producers of TGFβ which helps promote tumor progression.

Immunofluorescence of CD68/CD206 co-localization has demonstrated that M2 macrophages are present in 4T1 primary tumors of untreated, tumor-bearing mice. In the current study, there was an observed trend towards increased numbers of tumoricidal M1 macrophages in both primary tumors and lungs of 1D11 treated mice. Treatment with 1D11 did not lead to a significant decrease of two cell types, M2 macrophages and MDSC, associated with primary tumors. Although treatment with 1D1 did not lead to a decrease in the number of tumor-promoting M2 macrophages or MDSCs, there is a significant decrease of intracellular arginase from CD11b$^+$ cells isolated from both 4T1 primary tumors. This demonstrates pharmacodynamic activity of 1D11 in model because TGFβ has been shown to up-regulate arginase synthesis, produced by pro-tumorigenic M2 macrophages, and down-regulate synthesis of iNOS, which is produced by anti-tumorigenic M1 macrophages. Arginase has been shown to promote tumor cell proliferation, so inhibiting arginase production by neutralizing TGFβ could have detrimental effects on tumor proliferation and growth.

Example 4

Neutralization of TGFβ with the Pan-Neutralizing TGFβ Antibody, 1D11, Selectively Enhances the Efficacy of Chemotherapeutics in Preclinical Tumor Models The combination of TGF-β neutralization, using the murine monoclonal antibody 1D11, and select chemotherapeutics was tested in murine models of breast cancer, pancreatic cancer, melanoma, and renal cell carcinoma. Of the combinations tested, only the addition of 1D11 to the combinatorial therapy of capecitabine+ixabepilone consistently resulted in enhanced efficacy over the chemotherapeutic regimen alone. 1D11 routinely enhanced the efficacy of capecitabine+ixabepilone against primary tumor growth and inhibited metastasis in the syngeneic 4T1 subcutaneous (SQ) tumor model and is the first demonstration of additive effects when 1D11 is combined with chemotherapeutics in several studies of cancer.

1D11 was combined with paclitaxel in both a xenograft (MDA-MB-231) breast cancer model and the syngeneic 4T1 model of breast cancer. In these studies, 1D11 did not enhance the inhibition of primary tumors by paclitaxel, and in the 4T1 studies, 1D11 also did not enhance the ability of paclitaxel to inhibit spontaneous metastases from the primary tumors to the lungs. The combination of 1D11 and cyclophosphamide was also tested in the MDA-MB-231 xenograft model, and again, 1D11 did not enhance the efficacy of cyclophosphamide against primary tumor growth. The MDA-MB-231 and 4T1 models were also used to test combinatorial therapies with 1D11 and the platinum compounds cisplatin or carboplatin. In 4T1 SQ models, 1D11 did not enhance the efficacy of carboplatin against primary tumor growth. In a 4T1 model of experimental metastasis, where tumor cells are injected into the left ventricle of the heart resulting in metastatic seeding of the bones, adrenal glands, kidneys and lungs, both 1D11 and cisplatin were able to inhibit metastases particularly to the bone, but no enhanced efficacy was observed when the two therapeutics were combined.

No enhancement of efficacy was observed when 1D11 was combined with standard-of-care chemotherapeutics in models of pancreatic cancer or melanoma. Gemcitabine is the front-line chemotherapeutic for pancreatic cancer and the combination of 1D11 and gemcitabine was tested in a SQ xenograft model (Panc-1), a SQ syngeneic model (Pan02) and a genetically-engineered mouse model (GEMM) of Kras/mutant p53-driven pancreatic ductal adenocarcinoma (PDAC). In the Panc-1 studies, 1D11 had no effect on the efficacy of gemcitabine against SQ primary tumors, and a similar effect was observed in the PDAC GEMM. However, in the Pan02 model, combining 1D11 with gemcitabine actually reduced the efficacy of gemcitabine against primary tumor growth resulting in accelerated tumor growth when compared to controls.

The B16-F10 murine melanoma model was used to assess the effects of combining 1D11 with dacarbazine, the chemotherapeutic used as front-line therapy in melanoma. In a SQ B16-F10 model, 1D11 did not enhance the efficacy of dacarbazine against primary tumor growth. The chemocombo of 1D11 and dacarbazine was also tested in a spontaneous metastasis model of B16-F10 murine melanoma. In this model, tumor cells were injected subcutaneously into the plantar region of mice, where a primary tumor develops and metastasizes spontaneously to the regional popliteal lymph node. As in the SQ model 1D11 did not enhance the efficacy of dacarbazine against the primary tumors, and additionally did not enhance the efficacy of dacarbazine against metastasis to the draining lymph node.

Finally, 1D11 was tested in a Caki-1 renal cell carcinoma xenograft model in combination with cyclophosphamide and paclitaxel, and in this study, 1D11 appeared to reduce the effectiveness of each of these chemotherapeutics.

In summary, data clearly shows that neutralization of TGFβ with 1D11 only enhances the efficacy of specific chemotherapeutics. 1D11 enhanced the efficacy of the combination of capecitabine and ixabepilone in a preclinical model of breast cancer, but it did not enhance the efficacy of paclitaxel, cyclophosphamide, cisplatin, carboplatin, gemcitabine or dacarbazine in relevant tumor models.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A pharmaceutical composition to treat a breast cancer in a subject, comprising: a therapeutically effective amount of a Transforming Growth Factor beta (TGFβ) antagonist, capecitabine, and ixabepilone, wherein said TGFβ antagonist is present in an amount effective to enhance the efficacy of capecitabine and ixabepilone to treat said breast cancer.

2. The composition of claim 1, wherein said TGFβ antagonist is an agent that blocks the binding of a TGFβ protein to its receptor.

3. The composition of claim 2, wherein said agent is a protein.

4. The composition of claim 3, wherein said agent is an anti-TGFβ antibody.

5. The composition of claim 4, wherein said antibody is a pan neutralizing anti-TGFβ antibody.

6. The composition of claim 4, wherein said antibody is an anti-TGFβ monoclonal antibody.

7. The composition of claim 6, wherein said antibody is a humanized antibody that comprises one or more CDRs of 1D11.

8. The composition of claim 2, wherein said TGFβ protein is TGFβ-1, -2, -3, or a combination thereof.

9. A kit to treat a breast cancer in a subject, comprising: a therapeutically effective amount of a Transforming Growth Factor beta (TGFβ) antagonist, capecitabine, and ixabepilone, wherein said TGFβ antagonist is present in an amount effective to enhance the efficacy of capecitabine and ixabepilone to treat said breast cancer.

10. The kit of claim 9, wherein said TGFβ antagonist is an agent that blocks the binding of a TGFβ protein to its receptor.

11. The kit of claim 10, wherein said agent is a protein.

12. The kit of claim 11, wherein said agent is an anti-TGFβ antibody.

13. The kit of claim 12, wherein said antibody is a pan neutralizing anti-TGFβ antibody.

14. The kit of claim 13, wherein said antibody is an anti-TGFβ monoclonal antibody.

15. The kit of claim 14, wherein said antibody is a humanized antibody that comprises one or more CDRs of 1D11.

16. The kit of claim 10, wherein said TGFβ protein is TGFβ-1, -2, -3, or a combination thereof.

* * * * *